United States Patent [19]

Davis et al.

[11] Patent Number: 4,649,042

[45] Date of Patent: Mar. 10, 1987

[54] RUMEN DELIVERY DEVICE

[75] Inventors: Robert C. Davis, Greenfield, Ind.;
John W. Gibson, Birmingham, Ala.;
Daniel S. Skinner, Jr., Fountaintown,
Ind.; Timothy E. Dearth,
Indianapolis, Ind.; Dale C. Harris,
Fairland, Ind.

[73] Assignee: Eli Lilly and Company, Indianapolis, Ind.

[21] Appl. No.: 719,195

[22] Filed: Apr. 3, 1985

Related U.S. Application Data

[63] Continuation-in-part of Ser. No. 615,621, May 31, 1984, abandoned.

[51] Int. Cl.[4] .......................... A61K 9/22; A61K 9/30; A61K 37/24
[52] U.S. Cl. .................................................. 424/438
[58] Field of Search ....................... 424/16, 19, 20, 21, 424/22, 23, 26, 32, 33, 36

[56] References Cited

U.S. PATENT DOCUMENTS

| 3,887,699 | 6/1975 | Yolles | 424/19 |
| 4,251,506 | 2/1981 | Laby | 424/19 |
| 4,273,920 | 6/1981 | Nevin | 528/361 |
| 4,293,539 | 8/1981 | Ludwig et al. | 424/19 |
| 4,326,522 | 4/1981 | Guerrero et al. | 128/260 |
| 4,331,652 | 5/1982 | Ludwig et al. | 424/19 |
| 4,333,919 | 6/1982 | Kleber et al. | 424/15 |
| 4,381,780 | 5/1983 | Holloway | 424/21 |

FOREIGN PATENT DOCUMENTS

| 2059767 | 4/1981 | United Kingdom . |
| 2099699 | 6/1981 | United Kingdom . |

Primary Examiner—Morton Pollak
Assistant Examiner—Nathan M. Nutter
Attorney, Agent, or Firm—Joseph A. Jones

[57] ABSTRACT

An improved device for delivery of a medicament to the digestive tract of a ruminant animal comprises a polymeric medicated core retained in a dense tube by a relatively thick layer of an elastic sealant.

177 Claims, 23 Drawing Figures

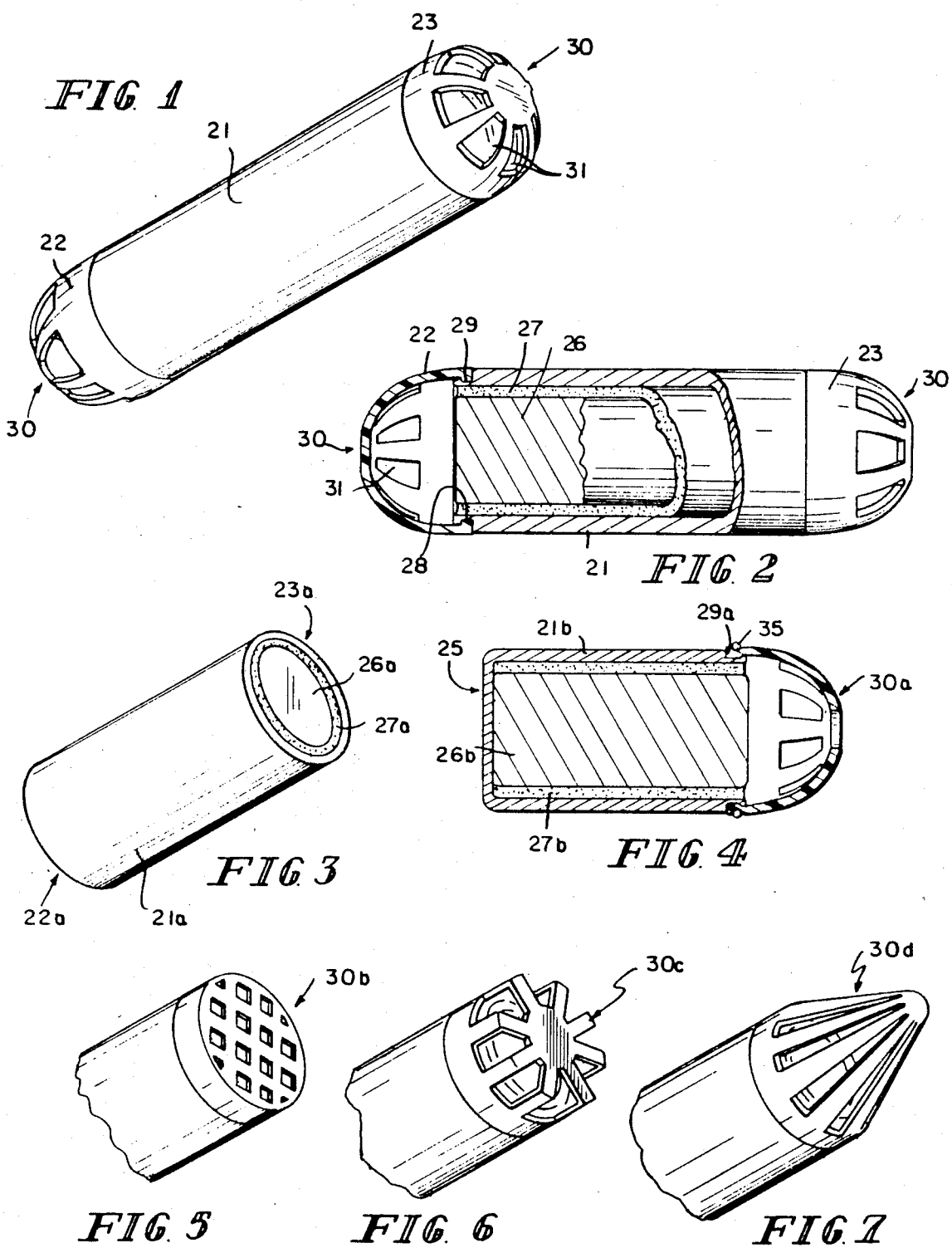

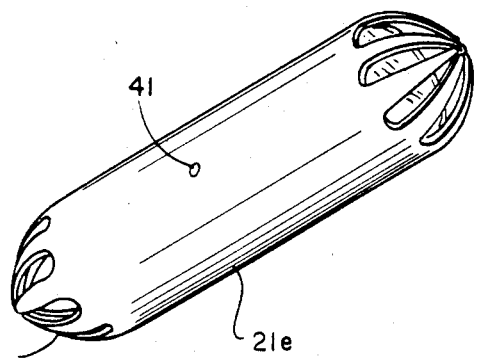
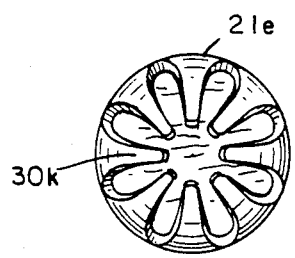
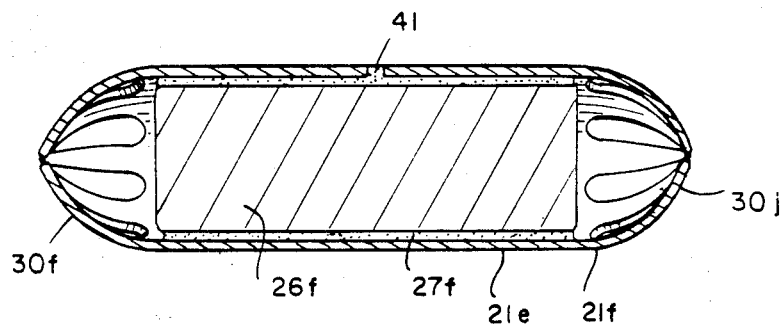

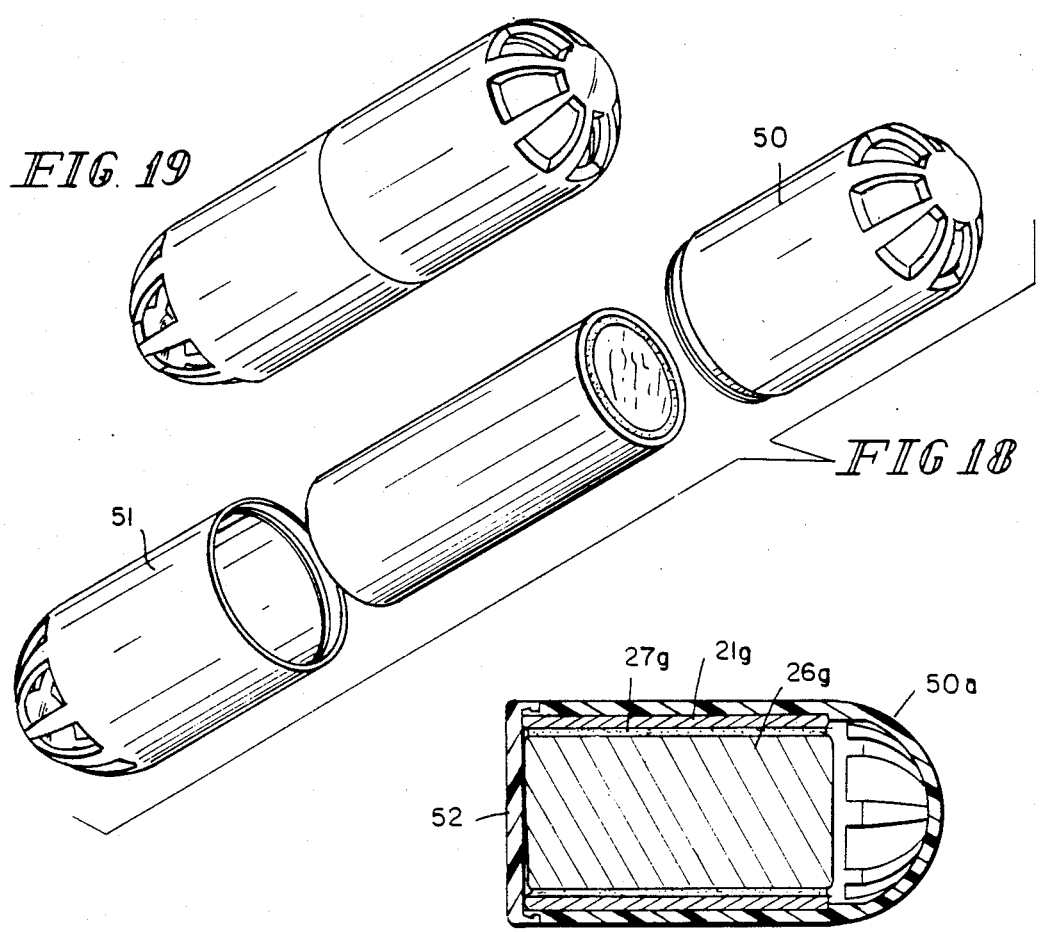
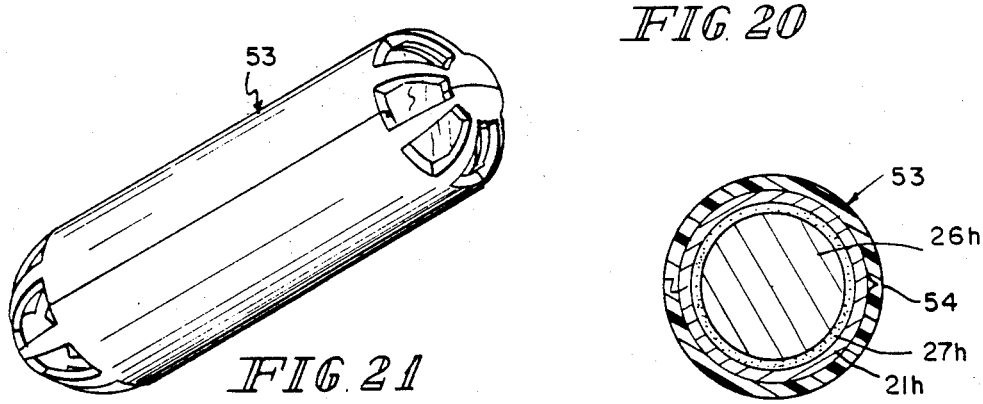

RUMEN DELIVERY DEVICE

CROSS-REFERENCE

This application is a continuation-in-part of copending application Ser. No. 615,621, filed May 31, 1984 and now abandoned.

BACKGROUND OF THE INVENTION

1. Field of the Invention

This invention belongs to the fields of animal husbandry and pharmaceutical formulation, and provides a device useful for the sustained delivery of a drug to a ruminant animal over a long period of time.

The problem to which the invention is directed is the delivery of drugs to the digestive tract of ruminants over an extended period of time. Of course, there is no problem in delivering such drugs to ruminants which are housed in a barn or feed lot; the drug is simply mixed with the animals' feed in the proper concentration. However, ruminant animals are frequently kept on pasture without supplemental feed for extended periods of time. Clearly, it is quite difficult to administer such drugs to non-supplemented pastured animals in effective doses. In the past, such drugs have been administered by mixing them with salt blocks, for the animals to lick, or by supplying a daily ration of concentrated feed in which the drug is mixed. Neither procedure is certain to give each animal its daily share of drug, and the latter procedure obviously requires effort on the part of the husbandman, and may be very difficult if the animals are widely dispersed in large pastures.

Thus, it would be desirable to have a better method of administering an orally-active drug over a very long period of time. For example, five months is about the longest period of time that most pasture land is capable of supporting animals in a growing condition, and that period of time is accordingly an approximate maximum period for the use of a rumen delivery device.

The drugs which are particularly desirable for delivery by such a device are the ruminant feed efficiency improvers, of which monensin is the most important. It was disclosed by Raun, U.S. Pat. No. 3,839,557, that monensin can be orally administered to ruminant animals to provide markedly improved weight gain per amount of feed consumed.

Other particularly important orally-administered compounds include anthelmintics, most especially the benzimidazole anthelmintics.

2. State of the Art

Ruminant animals are unique because their digestive tract includes a large vessel, the rumen and reticulum (referred to here collectively as the rumen), in which feedstuffs are held and fermented for a long period and which is continuously full of digesting feedstuffs. Thus, the possibility of retaining a delivery device in the rumen for a long period of time has been recognized and many expedients have been tried.

The primary problems are the design of a device which will mechanically be retained in the rumen, and the formulation of the drug in a form which will reliably release the desired dosage day by day over a long period of time.

The retention of the device has been approached from the aspects of density, and of geometric design. The latest and apparently best previous high-density device was that of Simpson, British Patent No. 2,059,767. That design comprises a core of polymeric drug matrix inside a steel cylinder. Both ends of the cylinder are open to the rumen, and the density of the device as a whole is so great, because of the weight of the steel cylinder, that the device remains at the bottom of the rumen and is not disturbed by movement of feedstuff in and out of the rumen.

Devices which are retained in the rumen because of their shape are typified by Laby's U.S. Pat. No. 4,251,506, showing a cylindrical device, open at one end, having extensible wings which are held closed while the animal is caused to swallow the device, and which open upon entering the rumen.

Both the devices of Simpson and of Laby are intended to produce uniform dissolution of a drug-laden matrix because a constant area—the end of a cylinder—is exposed to rumen fluid. It is obviously necessary to dissolve or suspend the drug in a substance which will dissolve or break down at a uniform rate in rumen fluid, if that approach is to be used. An excellent polymer for the purpose was disclosed by Nevin, U.S. Pat. No. 4,273,920. His polymer is composed of lactic acid and glycolic acid and is prepared by condensation of a mixture of those acids in the presence of a strong acid ion-exchange resin.

The problem with cylindrical delivery devices is that it is quite necessary for the container of the device to prevent any contact of rumen fluid with the walls of the cylinder of drug matrix. Consistent administration of the drug is possible only if the fluid contacts only the faces (or one face) of the cylinder and thus acts on a constant area throughout the life of the device. The problem, the art has found, is the difficulty of preventing leakage of rumen fluid between the drug matrix and the enclosing tube.

SUMMARY OF THE INVENTION

The present invention provides an improvement in sustained release drug delivery devices for use in the rumen of a ruminant animal of the type which comprises a polymeric core wherein the polymer comprises from about 60% to about 95% of lactic acid and from about 40% to about 5% of glycolic acid and has a number average molecular weight of from about 2000 to about 6000, in which a medicament beneficial when administered to the digestive tract of the ruminant animal is dissolved or suspended, which core is contained in a tube made of material with a density from about 6 to about 10 g./cc. which is compatible with the rumen, which tube has at least one end open for its full diameter, wherein the improvement comprises a relatively thick layer of elastic sealant filling the full length of the annulus between the core and the tube and forming an adhesive bond to both the core and the tube, which sealant is substantially impermeable to water, compatible with both the tube and the core, and compatible with and unaffected by the rumen.

DESCRIPTION OF THE DRAWINGS

FIGS. 1 and 2 represent the most preferred embodiment of the invention. FIG. 1 is a perspective view of the preferred embodiment, and FIG. 2 is a partial longitudinal cross-sectional view of it.

FIG. 3 is a perspective view of an embodiment of the same type, but without the end caps.

FIG. 4 is a longitudinal cross-sectional view of a third embodiment of the invention.

FIGS. 5–12 illustrate further embodiments of the invention.

FIGS. 15–17 show another embodiment of the invention; FIG. 15 is a longitudinal cross-section of it.

FIGS. 18–19 illustrate another embodiment in exploded and perspective views.

FIG. 20 is a longitudinal cross-sectional view of a further embodiment.

FIGS. 21–22 are perspective and crosssectional views of another embodiment, and FIG. 23 illustrates the outer shell of FIGS. 21–22 in open form.

DESCRIPTION OF THE PREFERRED EMBODIMENTS

All temperatures in this document are expressed in degrees Celsius, and all expressions of percentage, proportion and the like are in weight units unless otherwise stated.

Figure 10:
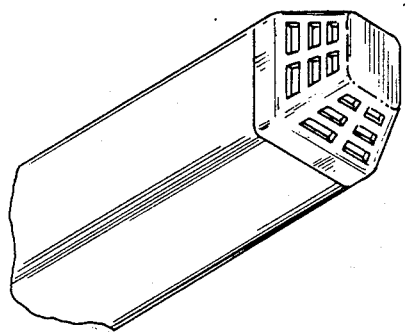

The device of the present invention is contained in a high-density tube, 21 in FIGS. 1 and 2. It is preferable to use cylindrical tubes, but other forms of tubes are permissible if desired. Square, as in FIG. 10, triangular or oval tubes can be effectively used, but are likely to be harder to form and fill than are cylinders. In choosing a tube, it must be borne in mind that the devices are orally administered to the animals to be treated, and accordingly the presence of sharp corners is obviously disadvantageous. If a square or triangular tube is to be used, therefore, it should be manufactured in such a manner that the corners are rounded off.

In a preferred embodiment, of FIGS. 1 and 2, the tube 21 is cylindrical and open at both ends 22 and 23, and the ends of the polymeric core 26 are approximately co-planar with the ends of the tube. The end caps 30 have perforations 31 and are of rounded cross-section. They are retained by a lip 28 which engages a groove 29 in the end of the tube.

The material of which the tube is made is governed by the requirements of high density and compatibility with the digestive tract. For example, lead would be an inappropriate material, despite its high density, for administration to domestic animals. The preferred tube materials are ferrous alloys, especially low-carbon steel and stainless steel. The various ferrous metals have densities in the general range of 7.0–7.9 g./cc., which provide devices of appropriate overall density.

It is desirable for a filled device according to this invention to have a density of at least 2.0 g./cc., and more preferable for the density to be in the general range from about 2.5 to about 5.0. It will be understood that, as the polymeric core, 26 in FIG. 2, is eroded away, the density of the device will increase because the density of the tube is higher than that of the core.

While the tubes may be made of any reasonable metal, such as, for example, nickel, tin, manganese, molybdenum and the like, economic and fabrication considerations make ferrous alloys by far the most preferable materials. At any rate, the material of the tube should preferably have a density of at least about 6 g./cc., up to about 10 g./cc. It will also be understood that the tube should be reasonably smooth on the exterior, to avoid injuring the animal while administering the device. Accordingly, wrought or extruded tubes are much more appropriate than cast materials. It has not been found necessary to coat the exterior of the tube for smoothness, since the surface finish of conventional metal tubing is smooth enough for ready administration.

The thickness of the wall of the tube need be only great enough to provide the necessary overall density, as well as sufficient strength for handling and administration. Tubing with walls in the range of about 1 to about 4 millimeters thick is appropriate, depending on the diameter of the device to be constructed. Preferably, devices to be administered to cattle are made of tubing with walls about 2–3 millimeters thick, and devices for smaller ruminants are made of tubing with walls about 1–2 millimeters thick. Another preferred range of wall thickness for cattle devices is about 1–3 millimeters.

Figure 11:
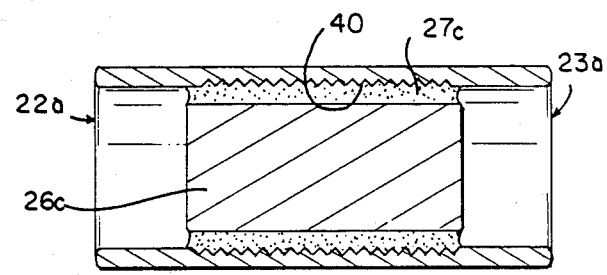

The inner surface of the tube may be abraded, grooved, roughened or textured, as shown at 40 in FIG. 11, to assist adhesion of the sealant 27c. Such preparation of the tube is not necessary, when the metal is properly prepared and the sealant is properly chosen, but is helpful and may be considered when the cost is not an obstacle. Any operation which will provide a mechanical feature on the inside of the tube will assist the sealant to bond to it. For example, the inside of the tube may be abrasive blasted to roughen it, or it may be grooved or threaded to provide relatively deep recesses into which the sealant will flow. It is preferred, however, not to roughen the inside of the tube but simply to use it as fabricated.

Either seamed or seamless tubing may be used, as is convenient and economical in the circumstances. Seamed tubing must be carefully prepared to avoid an excessively protruding seam which would interfere with the sealant layer. Further, unseamed tubing may be used. For example, tubing may be prepared by forming flat sheet into unseamed tubing. When the device is then assembled, the sealant is allowed to fill and seal the joint where the edges meet.

The size of a device according to the present invention is governed by the size of the animals to which it is to be administered, and by the amount of drug to be administered and the duration of administration. Although large cattle sometimes voluntarily swallow very large objects, the maximum length of the tubes of devices described here is about 85 millimeters. End caps 30, if used, can further extend the overall length of the device somewhat. The maximum diameter is about 40 millimeters.

If the cattle to be treated are calves of, for example, 150 kg., the maximum size of the device may well be smaller, such as 50 millimeters in length and 25 millimeters in diameter.

If the devices are to be administered to sheep or goats, they must obviously be quite small, such as in the range of about 10–20 millimeters in diameter and 25–35 millimeters in length.

The minimum size of a device depends on the daily dosage of drug and the duration of administration.

In general, the preferred size of the device for administration to cattle is from about 50 mm. to about 75 mm. in the length of the tube and core, and from about 25 mm. to about 40 mm. in outside diameter. The preferred size for administration to smaller ruminants is from about 10 to about 20 mm. in diameter, and from about 20 to about 35 mm. in the length of the tube and core.

It is preferred for the tube 21 and the core 26 to be substantially the same length, as in FIGS. 2 and 3. However, in certain instances it may be desirable for the tube to be longer than the core, as in FIG. 11, so that the wall of the tube overhangs and protects the ends of the core. In other instances, the core may be longer than the tube to allow faster drug delivery immediately after administration.

It is preferred for the tube to be open for its full diameter at both ends, 22 and 23, so that the core is eroded from both ends. However, there is no objection to using tubes closed at one end, 25 in FIG. 4, forming cups in effect, so that only one end of the core is exposed to erosion. It is more difficult to position the core and apply the sealant 27b in a tube which is closed at one end, but it is entirely possible to fabricate such devices and they may have an advantage, particularly when the desired administration rate is comparatively low.

It may be necessary or preferable to prepare or coat the inside of the tube to assist adhesion with the sealant. If the tube is made of stainless steel or nickel, or other low-iron-content metals, it is unnecessary to prepare the metal, except to clean it, because such metals have a stable surface. However, if the tube is made from a less inert metal, such as steel or oxidizable alloy steel, preparation of the surface for adhesion is necessary. Such metals may be plated with an inert metal, such as nickel, cadmium, chromium or tin. Less expensively and preferably, the metal may be coated with a film to eliminate corrosion and assist adhesion. The coating material, of course, must be compatible with the sealant, and with the rumen. Coatings and lacquers composed of a great variety of polymeric materials are available and may be used as is convenient in the circumstances with regard to the sealant to be used. For example, epoxy resins, polyethylene, phenolic resins, ethylene-vinyl acetate, polyvinyl acetate, nitrocellulose, acrylics and other coatings are appropriately used in various instances. Depending on the sealant to be used, it may be appropriate to use coatings based on rubber solutions, including silicone rubber or styrene-butadiene rubbers. The preferred coatings are polyethylene, vinyl polymers, including those comprising vinyl chloride, vinyl acetate and their copolymers, and acrylics.

Of course, any coating must be chosen with regard to the rumen environment, which is reducing, approximately neutral in pH, and conducive to hydrolysis, and must be safe to the animal and the consumer of the animal.

Still further particularly useful primers or coatings for metal tubes include those based on nitrile rubber, and mixtures of nitrile rubber and phenolic resins, as well as polyurethane lacquers and epoxy resins, including modified epoxies such as mixtures of epoxy with nylon, nitrile rubber or phenolic resins.

Coupling agents, especially silane coupling agents, are also useful in establishing a bond between metal and sealant that is impervious to moisture.

Figure 13:
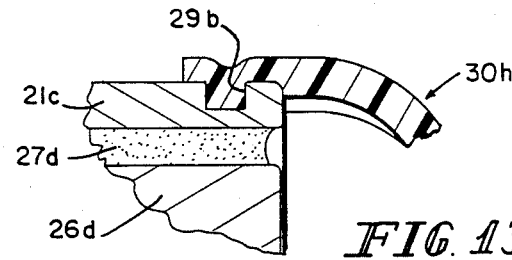
FIGS. 13 and 14 are enlarged views in cross section of two further embodiments of the present invention with respect to retaining an end cap in place.

If separate end caps, 30 in FIGS. 1 and 2, are to be used on the device, it may be necessary to prepare the tube in some manner to receive the end caps. For example, it is most preferred to groove the ends (or end, if the tube has only one open end) so that an end cap having an interior lip 28 is retained by snapping the lip into the groove 29. Other procedures are also appropriate, of course. For example, the end of the tube may be perforated, so that an inwardly-protruding peg on the end cap may be snapped or pressed into the perforation. Similarly, a deformable end cap may be used in combination with a tube having grooves 29b near the ends, and the assembly may be squeezed in a die to deform the material of the end cap into the groove, as in FIG. 13.

Still further, the outside diameter of the tube may be reduced by turning or pressing in a die, so that the end cap can fit the reduced diameter, providing a smooth outer surface for easier administration. FIGS. 1 and 2 of the drawings show such a preferred construction.

The embodiment of FIG. 4 uses a tube having one closed end 25, so that erosion and delivery of the medicament takes place from only one end of the polymeric core 26b. A variation of the end cap design 30a is shown, wherein a groove 29a is machined in the surface of the tube, and the end cap, made of a resilient substance, is pressed into the groove by a snap-ring or clamp 35.

It is preferred to use a perforated end cap over the open ends (or end) of the device. The end cap serves at least two purposes—it gives mechanical protection to the eroding face of the core, and it keeps the core in the tube in case the entire core, or a large piece of it, breaks free. Mechanical protection to the active face of the core is of some importance, since the rumen, particularly of a pastured animal, may contain considerable amounts of stones, pieces of wire and other debris which has been swallowed by the animal. Certain retention of the core in the tube is of considerable importance when the medicament may be toxic in excessive doses, as the ruminant feed efficiency improvers are. If the core, or a large piece of it, separates from the tube, it will probably be regurgitated and chewed up as the animal chews its cud, releasing all of the medicament in it at once. If a loose core is kept in the tube by the end caps, however, although the desired control over the release rate will be lost and the desired dose will be exceeded because of erosion from the sides of the core, it is unlikely that a toxic dose will be administered.

It has been found that the open area 31 of the perforated end cap is not an important variable. A desirable compromise open area, for devices about 35 mm. in diameter, is about 35–45%. Such an end cap provides adequate circulation to and from the eroding face, and is physically strong. However, end caps with open area as small as 18% have been found to be quite satisfactory, and mechanical strength is the only limitation on higher open areas.

The shape of the end cap may be chosen for convenience. It is most preferred to use an end cap of rounded shape, most preferably approximating a hemispherical shape, 30 in FIG. 1, because that shape is compact and easy to administer.

However, other convenient shapes are also appropriate for the end caps. They may be flat, as in FIGS. 5, 6 and 8 of the drawings, or they may be generally pointed, as in FIG. 7, or pyramidal, as in FIG. 10. Their shape is not critical, so long as the size and shape of the perforations is such as not to be easily occluded by particles of feedstuff and so long as the cap is physically strong enough to maintain its shape and position.

It has been observed in experiments that a certain amount of feedstuff always gathers adjacent the eroding face of the core, and that the space under the end cap may well be substantially full of it. This material seems to make no difference in the rate of erosion of the core, and accordingly in the rate of delivery of the medicament to the animal.

Figure 12:
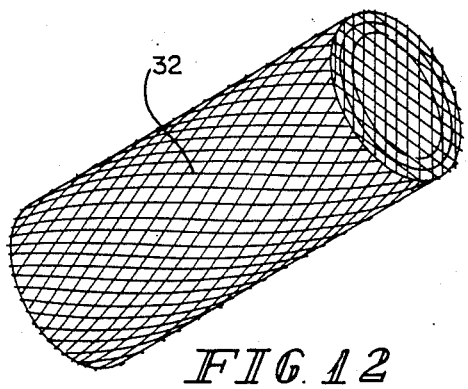

The end cap may be modified in many ways. For example, its function may be served by wrapping the entire device in a screen or mesh material, 32 in FIG. 12. The most convenient material for such a covering is heat-shrinkable plastic mesh tubing, which is placed over the device, tied or clamped at the ends, and shrunk in place. Such shrinkable plastic products are in common use.

Figure 8:
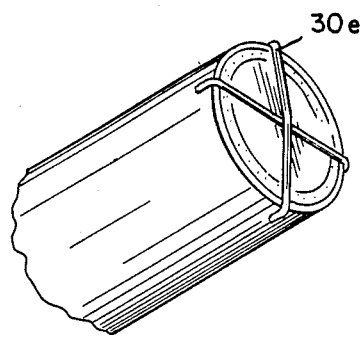

Alternatively, the open area of the end cap may be increased to maximum by forming it simply of one or a few pieces of wire, 30e, or other elongated members, fastened across the ends of the tube as in FIG. 8. Such an end cap obviously will not retain small pieces of the core in place, but will retain the core as a whole, if the bond between it and the tube fails. Wire end caps of this type may be applied by crimping the ends of the wires into perforations in the outside walls of the tube, or forming the ends of the wire or wires into a circular snap-ring, which is retained in a groove in the outside of the tube.

Similarly, a filamentary end cap may be made by eliminating all of a flat plastic end cap except the desired number of thin cross-members and snapping the end cap into place as has been described.

The material of end caps may be any relatively strong substance which is compatible with the rumen conditions. The preferred material is a readily molded plastic, such as polyethylene, either linear or crosslinked, polypropylene, polyurethane, polyvinyl chloride and the like. It is unnecessary to use the harder plastics, such as the melamines, phenolic resins, polycarbonates and the like, but they may be used if desired.

Figure 9:
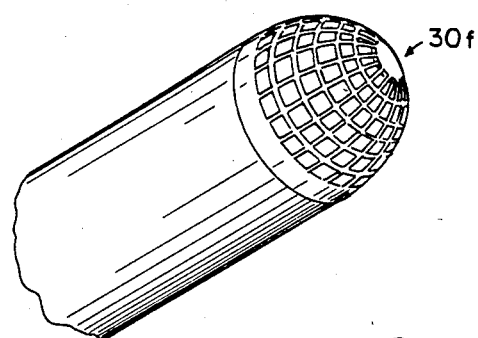

Of course, end caps may be made of metal, including aluminum, stainless steel, steel, plated steel such as tinplated, nickel-plated and the like, brass or any metal which is compatible with the rumen environment. Plain steel is acceptable for the end caps, because the rumen is not a very corrosive environment. Steel (or other metal) may be lacquered as has been described above to provide additional protection to the metal. Metallic mesh 30f may be used as shown in FIG. 9.

Various methods may be used to retain the end caps on the tubes, some of which are exemplified in the drawings. For example, the portion of an end cap overlapping the end of the tube may be forced into a groove in the tube by a snap-ring, or by tightening a clamp around it, 35 in FIG. 4. Of course, an end cap may be made to fit around the tube so tightly as to be retained by friction, but such a procedure is not recommended because the necessary close control of dimensions is not commensurate with the desired low cost of the devices.

Figure 14:
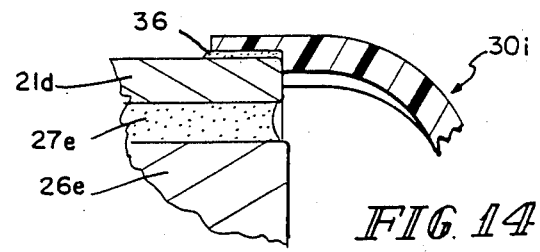

An end cap may well be retained by adhesive, 36 in FIG. 14, particularly since the tube must be capable of holding adhesive in order for the sealant to adhere properly. Suitable adhesives for adhering plastics to metals are common. In particular, the epoxy adhesives are compatible with most plastics and with the metals which are appropriate for the tubes. Metallic end caps may equally well be adhered with adhesives, and, again, the epoxy adhesives are particularly useful.

Still further, the tube and end cap may be threaded, and the cap retained in that way. Such assembly is particularly useful with metal caps, but plastic caps can also be threaded.

It is most preferred, however, to reduce the diameter of the end of the tube and to provide a groove 29 with a protruding lip, as indicated in FIG. 2, and to form the end cap from an elastomeric material in a design having a lip 28 which matches the groove and lip in the tube. In this manner, the end cap is assembled by merely snapping it over the lip on the tube, and a smooth device having tube and end cap of about the same outside diameter is provided.

Perforated end caps may also be economically provided by forming them as an extension of the same material which constitutes the tube. FIGS. 15-17 illustrate devices with such end-caps. It is preferred to form such a device by serrating the ends of a flat strip of metal to form fingers, 30j in FIG. 15, and to form the tube portion of the device by rolling up the flat strip and seaming it. It is possible, however, to form the fingers which make up the integral end-cap, 30k in FIG. 16, by cutting out the ends of a pre-formed metal tube.

When end-caps are provided as an extension of a tube, as shown in FIGS. 15-17, the "tube" of the device is the portion of the metal container which has a constant diameter, and the "end-cap" is the portion of the metal container which is reduced in diameter and provides open area for contact of the rumen fluid contents with the faces of the core. In FIG. 15, the tube is indicated by 21e and the end-cap by 30j, and the transition between them is indicated at 21f.

Another way to provide perforated end-caps is to enclose the entire tube in an outer shell, of which the end-caps are integral parts. FIGS. 18-23 illustrate such devices. The outer shells are preferably formed of plastic materials, and are preferably molded, because of the ease and economy inherent in the manufacture of such parts. The same types of materials which were discussed as materials for separate end-caps are also useful for outer shells; polyethylene is most preferred.

In FIG. 18, an outer shell is shown which is made up of two cylinders, each having an end-cap molded on one end. The halves of the shell, 50 and 51, are shown with a snap-joint to attach one to the other. It will be obvious, however, that the two halves of the shell may also be joined by welding, if made of an appropriate material. For example, polyethylene or polyurethane outer shells may be joined by heat-welding, as by spin-welding or by contact with a heated roller or open flame, by solvent-welding, or by a simple adhesive. When the parts of the shell are to be joined by welding, the ends 50 and 51 can be identical, providing a further economy in manufacture.

It will be understood that the core and tube which are enclosed by an outer shell with integral end-caps make up the simplest embodiment of the present invention, as shown in FIG. 3.

It will be further understood that an outer shell, as shown in FIGS. 18-23, need not be adhered to the tube in any way, but merely encloses and protects it.

FIGS. 18-23 illustrate outer shells wherein the end-caps are of approximately hemispherical shape, which is the preferred shape as has been discussed above. However, it should be understood that end-caps which are parts of an outer shell may have any shape, as discussed above and illustrated in FIGS. 5-10.

An outer shell may be used to reduce the dosage rate provided by a device, by opening only one end of the shell. FIG. 20 illustrates a device with an outer shell which has only one end-cap, the other end being closed off. The figure shows the closed end of the outer shell, 52, joined to the end capped end of the shell, 50a, by a snap-joint, but it will be understood that welding or adhesives are always appropriate, as well, to join the parts of the shell.

An outer shell may also be constructed by molding it in one piece, to be closed axially around the tube. Such a shell is shown in FIGS. 21-23. If such a design is to be used, the material obviously must be chosen with regard to the necessity to make an integral hinge, 54 in FIG. 23.

Polyethylene, again, is the preferred material for such shells. The onepiece shell is shown in cross-sectional view at FIG. 23, and a cross-section of the complete device is shown at FIG. 22. FIG. 21 shows the complete device in perspective.

Again, only a snap-jointed method of closing the outer shell is shown in FIGS. 21–23, but welding or adhesive closure of a one-piece shell is also appropriate and is even more preferred than in the shell of FIGS. 18–20, because of the length of the axial joint in a shell such as that of FIG. 21.

An axially-joined outer shell may also be made in separate halves, to be joined around the tube. The halves of such a shell would appear as in FIG. 23, with the two parts separated at the hinge 54. The halves may be joined by snap-joints or, preferably, by welding as discussed above.

The polymer which comprises the matrix portion of the polymeric core is the same polymer which was disclosed by Nevin in U.S. Pat. No. 4,273,920, the disclosure of which is herein incorporated by reference. The polymer is a copolymer of lactic acid and glycolic acid, and is composed of from about 60% to about 95% of lactic acid and from about 40% to about 5% of glycolic acid. Preferred copolymers are composed of from about 70% to about 90% of lactic acid, and the most highly preferred copolymer is composed of about 80% of lactic acid and about 20% of glycolic acid.

The polymerization is brought about, as taught by Nevin, with the aid of a strong acid ion-exchange resin at an elevated temperature. The average molecular weight of the copolymer is rather easily controlled by the reaction time and temperature. Nevin taught that the preferred average molecular weight was from about 6000 to about 35,000, more preferably from about 15,000 to about 30,000. His molecular weights are calculated by a gel permeation chromatography method, which provides weight-average molecular weights.

It has now been found preferable to calculate the average molecular weight from a titration, which measures the number of unreacted acid end-groups present and therefore gives a number average molecular weight. The analytical method is described below in Preparation 1. When the average molecular weight is determined in that manner, the preferred range is found to be from about 2,000 to about 6,000, more preferably, from about 2,000 to about 4,500, and most preferably, from about 2,500 to about 4,500.

Lower molecular weights provide higher rates of hydrolysis and therefore higher rates of release of the medicament. For example, one would use a higher-molecular-weight polymer for constructing a device open at both ends than for one open at one end only, for a given dosage rate. Further, one would use a higher molecular weight polymer if the concentration of medicament in the polymeric core were high, than if it were low, to provide a given administration rate. Obtaining the maximum duration of action from a given size of core requires a high molecular weight of the polymer, in order to deliver the medicament in a slow, sustained manner.

The preparation of the polymer is further explained by Preparation 1 below, which illustrates a large-scale polymerization.

The medicaments to be used in the polymeric core of the present devices are those which are beneficial to ruminant animals when orally administered. The most important and preferred medicaments are the ruminant feed efficiency improvers. Such compounds are now known to the animal husbandry art. The most important and preferred compounds of the group are monensin, narasin, taught by U.S. Pat. No. 4,038,384, of Berg et al., lasalocid and salinomycin. The feed efficiency benefit of the latter two compounds is taught by U.S. Pat. No. 3,794,732, of Raun, and U.S. Pat. No. 4,085,224, of Berg et al. Particularly preferred compounds are monensin and narasin. From another aspect, the most preferred compounds are narasin and salinomycin, because the daily administration rate of those compounds is considerably lower than that of the other ruminant feed efficiency improvers, and a given duration of action can therefore be obtained with a smaller device.

In most cases, it will be found that the medicament is soluble to some extent in the polymer, and the rest must be suspended and embedded in the polymeric matrix. Even complete insolubility of the medicament in the polymer provides perfectly satisfactory devices, because hydrolysis of the polymeric matrix releases particles of the medicament one or a few at a time, providing adequately continuous dosage of the medicament.

Anthelmintics constitute another class of medicaments which are particularly useful in the present devices. Such compounds must be administered in the digestive tract, because their purpose is to attack parasites inhabiting it. Typical and preferred anthelmintics are the class of benzimidazole carbamates, which are taught by U.S. Pat. Nos. 3,954,791, 4,154,846 and 4,156,006, which are herein incorporated by reference. A class of particularly preferred benzimidazole carbamates is described by the formula

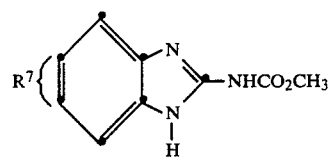

wherein $R^7$ is hydrogen, lower alkyl, lower alkoxy, lower alkylthio, benzoyl, halobenzoyl, phenylthio, phenylsulfinyl, cyclopropylmethylsulfinyl, and lower alkyl-$CO_2NH$. Particularly preferred benzimidazoles having the above formula are methyl-5(6)-phenylthiobenzimidazole carbamate, generically referred to as fenbendazole and methyl 5-propylthio-1H-benzimidazol-2-yl carbamate, generically referred to as albendazole. In the above formula defining benzimidazole methylcarbamates, $R^7$ defines a lower alkyl group such as $C_1$–$C_4$ alkyl, lower alkoxy such as $C_1$–$C_4$ alkoxy, lower alkylthio such as $C_1$–$C_4$ alkylthio, and lower alkyl-$CO_2NH$— such as $C_1$–$C_4$ alkyl-$CO_2NH$.

Compounds closely related to the above-mentioned benzimidazoles which also are useful in the devices include thiabendazole, which is 2-(4-thiazolyl)benzimidazole; levamisole, which is 6-aminophenyl-(2,3,5,6)-tetrahydroimidazo(2,1-b)thiazole; and febantel, which is N-(2-[2,3-bis(methoxycarbonyl)guanidino]-5-(phenylthio)phenyl)-2-methoxyacetamide.

Two other particularly valuable anthelmintics useful in the present devices are pyrantel, trans1,4,5,6-tetrahydro-1-methyl-2-[2-(2-thienyl)vinyl]pyrimidine, and diamphenethide, bis[β-(4-acetamidophenoxy)ethyl] ether.

Still another preferred anthelmintic is ivermectin, also called 22,23-dihydroavermectin $B_1$, U.S. Pat. No. 4,199,569 and *J. Med. Chem.* 23, 1134–36 (1980).

An animal scientist will understand that other classes of compounds are also usefully administered by the present devices. Any drug which is beneficial to ruminant animals when administered in the digestive tract, and which is administered at relatively small dosages for relatively long periods of time, is a candidate for administration in these devices. For example, compounds of which the dose is from about 1 mg./head/day to about 250 mg./head/day, for about 1–6 months, are advantageously so administered.

Besides the efficiency improvers and anthelmintics, particularly advantageous drugs include the antibiotics, such as tylosin, bacitracin, erythromycin, chlortetracycline and oxytetracycline; coccidiostats such as decoquinate; feed-through insecticides such as methoprene; ectoparasiticides such as the 2-fluoroalkylbenzimidazoles of U.S. Pat. No. 3,980,784; and estrus suppressors such as melengestrol. Further, the devices are particularly desirable for administration of trace elements and nutritional agents such as selenium, copper, magnesium, sulfur, iodine, vitamin A, vitamin D, vitamin E, and the B-complex vitamins.

The device must deliver the proper daily dosage of the drug or combination of drugs. Proper adjustment of the concentration of drug in the core, the area of the faces of the core, and the molecular weight of the polymer will readily provide any reasonable dosage. For example, 100 mg./day of monensin is provided by a core containing 40% drug which hydrolyzes 250 mg./day. Since the drugs to be used in the devices are known, and the proper dosages of them are in the literature, it requires only trivial experiments to determine the optimum concentration and molecular weight. The Examples below illustrate experiments which may be used as models.

It will be evident that a device which delivers both a ruminant feed efficiency improver and another drug could be very useful, and the present invention comprehends such combination devices. Narasin and salinomycin are quite highly preferred for use in combination devices, because of their activity at low dosage rates. Combinations of narasin or of salinomycin with fenbendazole, albendazole, or pyrantel are particularly preferred combination medicaments.

Further preferred combinations include monensin with melengestrol, monensin with ivermectin, and narasin or salinomycin with melengestrol or ivermectin.

The concentration of the medicament, or the combination of medicaments, in the polymeric core depends on the desired duration of activity and the hydrolysis rate of the polymer in which the medicament is dispersed. In any event, the maximum concentration of the medicament is about 50%, because of the necessity for the particles of medicament to be completely enveloped by the polymer. It is preferred to use maximum concentrations in the range of about 40%. Lesser concentrations, even as low as 1%, are used as may be convenient in formulating cores for use where the desired dosage rate is low, or where the duration of action which is needed is not particularly long.

The requirement of complete dispersion of the medicament in the polymer also calls for the medicament to be reduced to a fine particle size, and intimately mixed through the mass of polymer. Of course, if the medicament is soluble in the polymer, there is no problem with either particle size or mixing. However, if it is insoluble or only partially soluble, it is necessary to grind or otherwise pulverize the medicament to a particle size smaller than about 0.3 mm. (50 mesh). It is preferred to pulverize the medicament so finely that the largest particles are less than about 0.15 mm. (100 mesh) and it will be understood that the more finely the medicament can be ground, the more uniform a dosage rate can be obtained.

The mixture of polymer and medicament may be prepared in various ways. The polymer will soften at elevated temperature, and the medicament can be mixed through the softened polymer mass with powerful apparatus such as 2-roll mills, extruders and the like. The most convenient way to prepare the medicament is to grind both the polymer and the drug and to mix the two powders. The mixture is then heated to about 100°, at which point the polymer softens to form a mass which, upon cooling, becomes an amorphous material which may easily be ground. That coarsely ground material may then be charged to an extruder, run at an elevated temperature, which simultaneously mixes the material and forces it through a die. The material emerges from the die as a rod having the cross section of the desired core, and may be automatically cut to the desired length and cooled.

A particularly preferred way to form the cores is by first mixing the powdered drug with the coarsely ground polymer, and then pelletizing the mixture in an extruder. The pellets are collected and cooled, and used as feed for either an injection-molding machine, or another extruder. Injection-molding forms the desired cores directly. When a second extrusion is used, it is preferred to use the extruder to fill Teflon-lined molds to form the cores, or to extrude into a long Teflon-lined pipe, making a long rod of core material which is cut to core length when it has cooled.

If extrusion equipment which can provide intense mixing at low shear is available, the powdered drug and polymer can simply be mixed and fed to the extruder.

Other processes, of course, are equally practical. The polymer may be heated to soften it, the powdered medicament may be added, and the mixture may be vigorously mixed with equipment capable of mixing a heavy paste. The mixed polymeric mass may then be extruded to form cores, or may be poured into individual molds.

The polymer is soluble in some organic solvents, notably dichloromethane. If the medicament is soluble in the same solvent, both polymer and medicament may be dissolved and mixed, and the solvent then may be evaporated to leave a polymer-medicament mixture in extremely intimately mixed form. That mixture then may be extruded or molded with heat as described above.

Of course, if a medicament is used which is completely soluble in the polymer at the concentration used, the mixing operation is much less important. In such a case, it is only necessary to heat the polymer and mix the medicament with it, in such a manner that the medicament is in contact with the molten polymer for sufficient time to dissolve.

It is possible that some medicament could be added to the polymerization reactor, and thus combined with the polymer as it is formed. It is probable, however, that the high temperature and long time at temperature of the polymerization will unacceptably degrade any expected medicament.

The polymeric core is fixed into the tube with a relatively thick layer of a sealant. The function of the sealant is to provide a moisture-tight adhesive bond between the core and the tube, so that the sides of the core cannot be contacted by rumen fluid. It is the layer of sealant which provides the remarkable reliability of dosage administered by the present devices. In the absence of the sealant, devices of the prior art frequently failed, because fluid could infiltrate down the side of the core and hydrolyze the core, and therefore release the drug, from an uncontrolled area. Some individual specimens of prior art devices would perform well, hydrolyzing substantially only from the faces of the core, but other specimens, even from the same batch of devices, would hydrolyze uncontrollably and acceptable reliability was never obtained. It will be understood that a method of treating animals is of little value if the desired dosage is administered to only part of the treated animals, and the other animals get an uncontrolled dose.

Accordingly, the most important characteristic of the sealant is its ability to form a reliable adhesive bond with the polymeric core. The bond must be reliably formed over the entire surface of the core, and it must be moisture-tight.

Further, the sealant itself must be substantially impermeable to moisture, so that water from the rumen fluid cannot be absorbed into the sealant, and migrate through the sealant layer into the core. Of course, absolute impermeability cannot be achieved, but it is necessary that the sealant be sufficiently water-impermeable that no discernible hydrolysis of the copolymer occurs at the core-sealant interface. Equally, the sealant must be unaffected and unchanged by contact with rumen contents.

It is also necessary, of course, that the sealant be capable of adhesive bonding with the tube. That bond can be assisted by, for example, texturing or grooving the inside of the tube to provide mechanical gripping as well as adhesive bonding. As discussed above, the metal of the tube may also be coated to assist bonding. In addition, of course, end caps may be and preferably are used on the device, to retain the core in place if the sealant-tube bond fails. Nevertheless, best results have been seen when the adhesive bond between sealant and tube is strong and tight, and it is preferred to use sealants which bond to the tube as well as to the core. The sealant must be compatible with both the tube and core.

It is obviously necessary that the sealant be compatible with the rumen and safe to the animal, since the device is retained in the rumen for months. The safety requirement is easily met, because many types of sealants have been proven to be physiologically safe, and are approved for use in food packaging, for example.

The design of the device obviously imposes requirements on the sealant. It must cure or set in a relatively thick film, isolated from contact with air or other environmental influences. Polymers which cure with the aid of air or moisture, such as those silicones which set by hydrolysis of an ester, therefore can not be used. The sealant must be chosen from among those which can be applied in a molten state, and set as they cool, and those which are applied at ambient temperature and which cure by chemical action.

A degree of elasticity is a necessary property of the sealant. It appears that one of its major functions is to absorb relative movement between the tube and the core caused by thermal expansion and contraction.

Sealants, in general, are proprietary formulated products, which are worked out and perfected by specialists in polymers and adhesive technology. It is improbable that the volume of use of the present devices will justify the development of a new sealant formulation, and therefore it is more probable that an existing proprietary product, made for a larger-volume use, will be adopted. Accordingly, information about sealants from text books and the like is particularly important in the present case, and a particularly valuable one is Handbook of Adhesives, Irving Skeist, Ed., 2nd edition, Van Nostrand Reinhold (1977).

The hot-melt sealants are preferred. It is believed that the outer layers of the relatively lowmelting polymeric core are fused by contact with the hot-melt sealant, so that some amount of physical welding occurs as well as the adhesive bonding to the sealant.

Hot-melt sealants are usually chosen from those comprising ethylene-vinyl acetate copolymers, polyethylene resin, or polyamide resins. Ethylene vinyl acetate (EVA) is most preferred, and such copolymers are carefully discussed in Chapter 30 of Skeist. In general, such sealants, or adhesives as they are usually called, are based on a copolymer containing in the range of about 15-50% of vinyl acetate. The EVA copolymer must be modified with other ingredients, which may amount to as much as 50% of the sealant. For example, waxes, particularly microcrystalline waxes, are added to lower the viscosity of the molten sealant, and tacky polymeric materials such as polybutenes are added to improve its initial tack for easier assembly of the tube and core. It may be advisable to add an antioxidant to inhibit high-temperature degradation of the sealant; butylated hydroxy toluene and butylated hydroxy anisole are useful antioxidants.

EVA copolymers may be mixed with selected low molecular weight resins for improved adhesion, wetting, tackiness and strength at elevated temperatures. Among suitable resins are methyl styrene copolymers, rosin esters and polyterpene resins.

In general, waxes may be used in amounts up to about 20%, of which microcrystalline waxes should comprise the greatest part. Plasticizers may also be used in amounts up to about 20%, and modifier resins, as discussed above, are used in amounts in the range of from about 20% to about 50%.

Inert, inorganic fillers are sometimes used in such sealants, but preferably are not, and certainly should not be used in amounts above about 20% of the sealant.

The melting, or more accurately softening, temperature and the viscosity of hot-melt sealants in general, and EVA sealants in particular, are adjusted by varying the molecular weight of the polymer and the composition of modifying ingredients. In the present application, it has been found best to use hot-melt sealants having moderate viscosity in the molten state, such as from about 800 centipoises to about 10,000 centipoises at the application temperature, preferably, from about 800 to about 3,000 centipoises.

Excessive application temperatures should be avoided, because of the relatively low melting point of the polymeric cores and the heat sensitivity of the medicaments. In general, application temperatures in the range of from about 120° to about 175° are advisable.

Hot-melt sealants based on polyolefin resins, preferably polyethylene resins, are widely used and are available, for example from Eastman Chemical Products, Inc., Kingsport, TN, U.S.A., under the trademark Eastobond. Such sealants are formulated from the polyolefin resin, modified with microcrystalline wax to improve the viscosity and hot tack properties.

A third major class of hot-melt sealants which are appropriately used in the present devices are the polyamides, which are polymers made by condensing a diamine, generally ethylenediamine or a similar small alkylene compound, with a high-molecular weight dibasic acid. Most commonly the acid is "dimer acid", wherein the two carboxy groups are joined by a 34-carbon (average) hydrocarbon group containing a number of unsaturated bonds. Polyamides give particularly good adhesion, apparently because of their excellent ability to wet relatively nonporous substances, such as the tube of the present devices, and have particularly good stability in storage. The polyamide sealants require less formulation to achieve excellent results than do the other chemical types of sealants which have been discussed.

Another class of hot-melt sealants useful in the present devices are those based on thermoplastic rubber. Such rubbers are based on polymers having both rubbery and plastic constituents, usually block polymers made up of styrene and butadiene, or of styrene and isoprene. The polymers are made up in such a way that the macromolecule terminates with glassy end blocks, of polystyrene, which are incompatible with the rubbery isoprene or butadiene mid blocks. Thus, the polystyrene end blocks tend to cluster together and form domains which lock the rubber chains in place. When the thermoplastic rubber is heated above the transition temperature of the end blocks, the polymer becomes flowable and can be extruded or otherwise forced into small openings, such as the annulus between core and tube of the present devices.

The styrene-diene block copolymers may be formulated with low molecular weight resins or plasticizers. Aromatic resins, for example styrene homologue copolymers, tend to associate with the hard styrene end-block domains. On the other hand, low molecular weight olefin resins, rosin esters and polyterpenes gravitate to the diene midblocks, improving tack. Among liquid plasticizers, the polybutenes also are miscible with the midblock phase. Additional types of sealants, other than the preferred hot-melt types, include those which can be applied and caused to set or cure by chemical methods. Of course, it is impossible to use sealants which are applied as solutions or dispersions in a solvent, or in the form of emulsions, because the solvent or water can not escape from the long, confined space in which the sealant must be deposited. Therefore, sealants other than hot-melt types must be of the varieties which set by chemical action and which release nothing, even water, as they cure.

Sealants which are applied at approximately ambient temperature and cure in place by chemical action are quite useful. The silicone sealants are particularly desirable for the purpose. Such sealants are presently in wide use, particularly in the construction and electrical industries. They are composed of a linear polydimethylsiloxane polymer, containing in the range of 300 to 1600 dimethylsiloxane units, and a polyfunctional silane which is cross linked by condensation with the aid of a catalyst. The usual catalysts are tin or titanium compounds, particularly soaps such as stannous octoate, dibutyl tin dilaurate and the like. The condensation and polymerization will take place in an anaerobic location such as the present sealant layer when the condensation catalyst is separate from the functional silane until just before the sealant is applied to the device.

The polysulfide sealants are in very wide use for assembly of glass to metal, wood to metal and the like. They have also been used as dental impression compounds and therefore have been shown to be safe for physiological purposes. The sealants are solidified to form flexible, elastic polymers by the polymerization of thiol-terminated units of the general formula $$HS(C_2H_4OCH_2OC_2H_4SS)_nC_2H_4OCH_2OC_2H_4SH$$

having a molecular weight averaging around 4,000.

The catalysts for polymerizing polysulfides are oxidizing agents. Lead dioxide is most widely used but has an obvious disadvantage in the present application. However, manganese dioxide, zinc peroxide, and so forth are also useful oxidizing agents and may be used here.

A polysulfide sealant would be used for the present purpose by mixing the monomer with the oxidizing agent immediately before assembly of the devices, injecting the sealant preparation into the annulus between core and tube, and allowing the assembled device to stand until the polymer had set. The polysulfides are known for their water resistance and ability to withstand large amounts of thermal expansion and contraction, and therefore are rather particularly appropriate for the present application.

It will be understood from the foregoing discussion that the chemical nature of the sealant is entirely unimportant to the success of the present devices, so long as it is compatible with the tube and core. The physical properties of the sealant are vital and may be obtained from a wide variety of chemical entities. The necessary physical properties, in summary, include the ability to form a moisture-tight adhesive bond to the polymeric core and to the tube, and a high degree of water-impermeability to prevent permeation of water through the layer of sealant to the sides of the core. It is also necessary that the sealant be sufficiently cohesive and elastic to absorb relative movement of the core and tube during thermal expansion and contraction over the temperature range encountered in storage and use, from about −20° to about 50°.

The sealant is used in a relatively thick layer, filling the full length of the annulus between the core and the tube. The term "relatively thick" means a layer of, at least, 0.7 mm. thickness, and preferably from about 2 to about 4 mm. in thickness. Another preferred range of thickness of the sealant layer is at least 1 mm. in thickness. Of course, smaller devices for use in sheep or goats can be made with a thinner layer of sealant, but the sealant should always have a thickness of at least several percent of the diameter of the core, for example, from about 3% to about 20% of the diameter, preferably from about 5% to about 20% of the diameter.

The formulation and preparation of the polymeric core has been discussed above. The core is assembled in the tube in any manner which allows the core to be placed approximately concentric with the tube, and the annulus filled with the sealant. Exact concentricity is not necessary, because the thickness of the layer of sealant does not control the dosage rate. A tolerance of, for example, 0.5 mm. in the concentricity of the core and tube is allowable. Accordingly, it is unnecessary to assemble the devices one at a time. A long rod of core material may be extruded or molded, for example, 1 meter long, and may be placed inside a tube of the same length in a fixture which holds the core in place in the tube. The sealant, whether hot-melt or chemically curing, is then injected into the annulus, the assembly is set aside to cool or cure, and is cut to the proper lengths for the desired devices.

It is preferred, however, to cut the tube and core extrusion or casting into lengths suitable for individual devices, and to place each core in its tube in a fixture which holds it in place while sealant is injected into the annulus. The injection equipment sold under the trademark Slautterback is particularly appropriate for the purpose. The assembled device is held in its fixture while sealant cools or cures. Obviously, less fixtures are necessary when quick-setting hot-melt sealant is used, providing a significant advantage in the use of hot-melt sealant.

When a tube with integral end-caps is used, such as the device of FIGS. 15–17, it is obviously difficult to inject sealant from the end of the annulus. It is preferred to drill or punch a small hole in the tube, 41 in FIGS. 15 and 17, and inject the sealant through it. The hole must be sealed closed, as by an excess of sealant or by covering it with a water-proof coating or sticker.

After the sealant has cooled or cured, it is advisable to inspect the ends of the device to assure that part of the face of the polymeric core is not covered by sealant which has flowed out of the annulus spread across it. It may be advisable to face the open end or ends of the device on an abrasive belt or the like to assure that the full diameter of the core is available to contact with rumen contents.

The final operation in assembly of the devices is to apply the end cap or caps, if separate end caps are used, or the outer shell including end caps, or to close up the metal fingers which constitute integral end caps. The fingers may be closed tightly, as in FIG. 15, or loosely, as in FIG. 16. The tube or outer shell may be labelled with ink or paint, or a separate rumen-acceptable label may be applied. For example, the label may be printed on a tube of shrinkable plastic material, and shrunk to fit permanently around the tube or outer shell.

The devices are administered to ruminants orally, usually using a balling gun to introduce the device into the animal's throat behind the tongue. A device usually lodges in the reticulum and remains there.

The following examples of the construction and use of typical devices of the present invention are provided to assist the reader in making use of the invention to the best advantage. The first preparation illustrates the large scale synthesis of the polymer.

Preparation 1

To a 50-gallon jacketed reactor equipped with a condenser and means to return condensate to the reactor or to remove it, as well as with vacuum and pressure equipment, were added 100 kg. of 88% aqueous lactic acid (80 mole percent) and 30 kg. of 70% aqueous glycolic acid (20 mole percent). To the mixture was added 1.3 liters of Dowex acid exchange resin HCR-W2-H, and the mixture was heated to 130° over a period of 4 hours. The water which was released from the polymerizing mixture was removed in the condenser and discarded.

After the temperature had reached 130°, the pressure in the reactor was slowly reduced over a period of 15 hours, while the temperature was increased, to final values of 160° and 70 mm. Hg. Care is necessary to prevent violent boiling in the reactor while the pressure is reduced, and the operator must observe the mixture frequently and inject nitrogen in the reactor as necessary to depress foaming.

After 15 hours, the reactor was brought back to atmospheric pressure and the collected water was discarded. The condenser was then connected to steam to prevent plugging in it, and cooling brine was circulated through the jacket of the receiver from the condenser. The vapor lines were heated with steam to prevent any plugging in them. The temperature in the reactor was then raised slowly from 160° to 170°, while the pressure was slowly reduced to 20 mm. Hg. The polymerization mixture was held at that temperature and pressure for 22 hours.

The temperature was then raised to 185° over a period of 4 hours, while the pressure was decreased to less than 5 mm. The mixture was then held at 185° for 40 hours, and was periodically sampled. The inherent viscosity of the samples was determined with an Ubbelohde viscometer by dissolving an aliquot of the polymer in chloroform at 0.5 g./100 ml. The inherent viscosity is the natural logarithm of the ratio of the efflux time of the polymer solution to the efflux time of pure solvent, divided by 0.5. The end point inherent viscosity of the polymer obtained was 0.16 dl/g.

The polymer was then screened through a 60-mesh stainless steel screen to remove the catalyst beads, was poured out into stainless steel trays to cool, and finally was broken up in pieces for storage. The yield of the process was 65 kg. of polymer.

Analytical Method

The number average molecular weight of polymers prepared as in Preparation 1 is determined by titrating a sample of the polymer with base. The method assumes that each molecule of polymer has one carboxyl end group. An accurately weighed sample of approximately 1 g. of polymer is dissolved in about 250 ml. of chloroform, and 15 drops of 0.1% phenol red indicator in methanol is added. The titrant is 0.1N sodium hydroxide in methanol, prepared by dissolving 4 g. of analytical grade sodium hydroxide in about 5 ml. of water, and diluting the solution to 1 liter with methanol. The titrant is standardized in the usual way against a standard acid substance such as potassium biphthalate.

The polymer sample is titrated in the usual way to measure the millimoles of base equivalent to the weight of polymer sample, and the average molecular weight of the polymer is calculated from that value.

The batches of polymer used to prepare the devices in the examples below were analyzed according to the above method, and the molecular weights so determined are reported here.

EXAMPLES 1–6

A group of six different types of devices were prepared for testing in cattle. The same medicated polymeric cores were used in all six types.

Polymer was prepared according to the process of Preparation 1. Its number average molecular weight was 3,000. It was ground to a particle size less than 0.18 mm., and 60% by weight of the ground polymer was mixed with 40% by weight of powdered monensin, sodium salt. The mixture was heated for 2 hours at 95°, and the sintered mass was cooled and ground to less than 3 mm. particles in a hammermill.

Cores were formed from the granulated mixture by extruding it through a Killion extruder fitted with a 19 mm. barrel 380 mm. long into Teflon molds to prepare 25 mm. diameter cores, 58 mm. long. The extruder was operated with the addition zone at 50°, the heating zone at 88° and the die at 160°. The pressure at the die end of the compression zone was 1,000–1,500 psi, and the molds were at ambient temperature.

The tubes used to assemble the devices were round seamless tubes weighing 99 g. each. The outside diameter was 35 mm., the inside diameter, 30 mm., and the length 50 mm.

The tubes used in Examples 1, 3 and 5 were of type 304 stainless steel and were cleaned with soap and water ultrasonically and degreased ultrasonically with dichloromethane. The tubes in Examples 2, 4 and 6 were mild steel, and the inside of the tubes was prepared by sand blasting and cleaning as above.

A Slautterback injector was used to assemble the devices by injecting molten hot-melt sealant into the annulus between the tube and core. The tube was preheated to 60°–80° and the core was at ambient temperature when assembled, and the sealants were injected at 175°–190°. The devices were allowed to stand until cool, and the protruding ends of the cores and excess sealant were sanded off on an abrasive belt so that the core ends were coincident with the ends of the tubes.

Three hot-melt sealants were used. The sealant in Examples 1 and 2 was Eastobond A-110S; in Examples 3 and 4, Eastobond A-337S, and in Examples 5 and 6, Allied CH-35.

The two Eastobond sealants are products of Eastman Chemical Products, Inc., and comprise polyethylene modified with microcrystalline wax. The viscosity of A-110S is 2200 centipoises at 163°, and its ring and ball softening point is 96°. The viscosity of A-337S is 2300 centipoises at 163°, and its ring and ball softening point is 95°.

Allied CH-35 is manufactured by Allied Adhesive Corp. of Richmond Hill, New York, N.Y., U.S.A. and is composed of DuPont ethylene-vinyl acetate resin, a styrenic resin supplied by Hercules Inc., Wingtack polymerized mixed olefins manufactured by the Goodyear Chemical Co., amorphous polypropylene supplied by Moore and Munger, Fairfield, Conn., microcrystalline wax, and Paraflint synthetic wax supplied by Moore and Munger. Its viscosity is 900 centipoises at 175°.

Test I

The devices of Examples 1–6 were administered to fistulated cattle to determine the manner in which the devices released the drug. The cattle were of mixed breeds, and ranged in weight from 900 to 1400 pounds. Each animal had a fistula surgically implanted in the rumen so that the devices could be placed in the reticulum and removed at will. Two devices were placed in the reticulum of each animal to start the experiment. Ten devices of each lot were tested.

The study was carried out at a research farm in Texas, U.S.A., during the late winter and spring. The pasture on which the animals were fed consisted of native grass, and the animals were rotated to fresh pasture as necessary. Grass hay was fed when the ground was snow-covered.

At intervals of approximately two weeks, all of the devices were removed from the animals, rinsed, dried with paper towels, and weighed. The loss in weight from the core was determined, and the amount of drug released was calculated from the weight loss and the known percentage of drug in the core. A device was not returned to the animal if serious uncontrolled erosion of the core was seen, for example, if erosion was proceeding down the walls of it rather than on the face. Some devices were also removed from the test for study.

The results of the test are shown in the table below. For each measurement interval, the average dosage of drug per day for the interval preceding the measurement is shown, together with the standard deviation. The number of devices still in the test is shown in parentheses for each measurement interval. Six of the devices of Example 3 and eight of the devices of Example 4 were taken out of the test at the 69-day measurement because they were failing due to apparent failure of the sealant-core bond with resulting uncontrolled erosion.

TABLE I

| | INTERVAL MEAN RELEASE RATES, MG. MONENSIN SODIUM DAY + SD | | | | | |
|---|---|---|---|---|---|---|
| | OBSERVATION DAY | | | | | |
| Treatment | 14 | 28 | 42 | 56 | 69 | 84 |
| Ex. 1 | 37 ± 12(10) | 79 ± 16(10) | 77 ± 12(10) | 85 ± 11(10) | 111 ± 10(10) | 128 ± 10(9) |
| Ex. 2 | 41 ± 13(10) | 86 ± 21(10) | 74 ± 14(10) | 92 ± 13(10) | 119 ± 18(10) | 127 ± 14(8) |
| Ex. 3 | 43 ± 12(9) | 90 ± 14(9) | 66 ± 11(9) | 94 ± 11(9) | 113 ± 24(9) | 203 ± 49(3) |
| Ex. 4 | 45 ± 17(9) | 79 ± 34(9) | 71 ± 8(9) | 89 ± 10(9) | 100 ± 15(9) | 108(1) |
| Ex. 5 | 39 ± 17(10) | 92 ± 20(10) | 65 ± 22(10) | 90 ± 21(10) | 88 ± 18(10) | 114 ± 17(10) |
| Ex. 6 | 38 ± 18(10) | 96 ± 33(10) | 71 ± 10(10) | 87 ± 15(10) | 99 ± 25(10) | 193 ± 99(9) |

Test II

Another test of devices of Examples 1–6 was carried out in fistulated steers on pasture near the Gulf coast of Texas, U.S.A. from February through May. The pasture consisted of lush oat and ryegrass forage during the trial period, and was judged to provide more feed than needed by the animals. Thirty-nine steers were used in the study, and two devices were administered to each steer, so that thirteen devices from each of the six lots were tested.

The devices were initially administered orally to the fistulated animals, using an appropriate balling gun. The location of the devices in the rumen or reticulum was noted each time the devices were removed, and they were replaced after weighing in approximately the same location. In almost all cases, the devices were located in the reticulum, not in the rumen.

The results, reported as in Table I, were as follows.

TABLE II

INTERVAL MEAN RELEASE RATES, MG. MONENSIN SODIUM/DAY ± SD

| Treatment | OBSERVATION DAY | | | | |
|---|---|---|---|---|---|
| | 14 | 28 | 56 | 74 | 92 |
| Ex. 1 | 39 ± 16(13) | 87 ± 15(13) | 119 ± 25(13) | 126 ± 39(13) | 108 ± 39(10) |
| Ex. 2 | 44 ± 8(13) | 86 ± 8(13) | 122 ± 27(13) | 136 ± 52(13) | 146 ± 63(11) |
| Ex. 3 | 48 ± 9(13) | 81 ± 15(13) | 121 ± 23(13) | 112 ± 29(13) | 70 ± 42(11) |
| Ex. 4 | 45 ± 15(13) | 83 ± 15(13) | 147 ± 30(13) | 167 ± 64(13) | 137 ± 16(3) |
| Ex. 5 | 45 ± 12(13) | 81 ± 13(13) | 109 ± 11(13) | 91 ± 28(13) | 72 ± 29(13) |
| Ex. 6 | 48 ± 11(13) | 86 ± 10(13) | 118 ± 42(13) | 150 ± 58(11) | 146 ± 58(5) |

It will be observed that the dosage rates in Test I are consistently lower than those in Test II. It is believed that the difference is caused by the difference in the forage of the cattle. It appears that the lush, moist forage of the cattle in Test II resulted in higher dosage rates, presumably because of the greater amount of free water in the rumen of those cattle.

It is also apparent that the uncoated steel devices of Examples 2, 4 and 6 gave greater variability and higher dosage rates than did the stainless steel devices of Examples 1, 3 and 5.

EXAMPLES 7-8

Two lots of devices were made, using a polymer substantially the same as that used in Examples 1-6. The medicament in Example 7 was regular production monensin sodium, used at 40% of 90.4% pure compound with 60% of polymer. Example 8 contained 40% of 95.2% pure recrystallized monensin sodium, used with 60% of polymer. The polymer-drug mixture was prepared as described above in Examples 1-6.

The cylinders in all of these examples were type 304 stainless steel, with the inside surfaces grooved to assist adhesion. The tubes were cylindrical, of the same size used in Examples 1-6.

The polymeric cores were formed with the same extruder and Teflon mold used in Examples 1-6. The extruder was operated at 60 rpm, with the feeding zone at 80°, the heating zone at 138° and the die at 120°. The melt left the die at 126°-127°.

The sealant was Eastobond A-337S. The assembly of the devices was carried out as described in Examples 1-6.

Test III

A group of 36 fistulated Holstein and crossbred steers weighing between 700 and 1,000 pounds was used to test the devices of Examples 7-8. The experiment was carried out in central California on pasture consisting of about 80% improved forage species and 20% native forages. The pasture was irrigated and the steers were moved from one pasture to another as needed to maintain the quality of forage.

Two devices were placed in the reticulum of each steer through the rumen fistula to begin the test, and the devices were removed, inspected and weighed, substantially as described in Test I above. Individual devices were sometimes not weighed because they could not be found in the rumen contents.

The following table reports the dosages observed in the test.

TABLE III

INTERVAL MEAN RELEASE RATES, MG. MONENSIN SODIUM DAY ± SD

| Observation Day | TREATMENT | |
|---|---|---|
| | Ex. 7 | Ex. 8 |
| 27 | 74 ± 6(8) | 82 ± 8(8) |
| 39 | 73 ± 18(9) | 75 ± 22(9) |
| 56 | 92 ± 8(9) | 110 ± 24(9) |
| 70 | 93 ± 9(9) | 143 ± 26(9) |
| 84 | 114 ± 25(9) | 109 ± 17(8) |
| 98 | 125 ± 66(9) | 204 ± 45(8) |
| 110 | 186 ± 31(7) | — |

Test IV

The devices of Examples 7-8 were tested in another group of Holstein and cross-bred steers, weighing between 750 and 1,335 pounds, on an improved pasture in the same district of central California. The forage was similar to that of Test III, except that this test was carried out during the winter, and it was necessary to supplement the steers with oat, hay and corn silage from time to time. The devices were evaluated as described in the tests above, and the following dosage rates were observed.

TABLE IV

INTERVAL MEAN RELEASE RATES, MG. MONENSIN SODIUM/DAY ± SD

| Observation Day | TREATMENT | |
|---|---|---|
| | Ex. 7 | Ex. 8 |
| 11 | 53 ± 39(12) | 75 ± 21(12) |
| 25 | 79 ± 7(12) | 83 ± 10(12) |
| 39 | 94 ± 14(12) | 101 ± 13(12) |
| 60 | 98 ± 16(12) | 111 ± 13(12) |
| 75 | 125 ± 24(12) | 136 ± 33(12) |
| 89 | 124 ± 45(11) | 217 ± 78(11) |
| 102 | 195 ± 33(7) | 118(1) |

EXAMPLES 9-14

Four variables were evaluated in the tests of these six examples.

The polymer was of the same type described in Preparation 1, and two lots of polymer having different molecular weights were used. The number average molecular weights were 2,800 and 4,400, respectively.

In all cases, the medicament comprised 40% of 90.2% pure monensin sodium, mixed with 60% of polymer. The polymer and drug were mixed and the mixture was extruded to form molded cores, as described above in the preparation of Examples 1-6.

The tubes were type 304 stainless steel seamless tubing, of the dimensions described under Examples 1-6, except that some of the examples used tubes and cores which were 76 mm. long.

Some of the examples were finished with polyurethane end caps of the design shown in FIG. 1, having an open area of 38%. The caps were retained on the tube by molded lips snapped into corresponding grooves, as shown in FIG. 2.

Two types of hot-melt sealant were used in these examples. Some were assembled with Allied CH-35, and some with Eastobond A-337S, as indicated in the table below. In all cases, the sealant was injected at high temperature as described under Examples 1–6.

The following table indicates the variables used in assembling each example.

| Example | Length | Molecular Wt. | Caps | Sealant |
|---|---|---|---|---|
| 9 | 50 mm. | 2800 | no | A-337S |
| 10 | 50 | 4400 | no | CH-35 |
| 11 | 50 | 4400 | yes | A-337S |
| 12 | 50 | 2800 | yes | CH-35 |
| 13 | 76 | 4400 | no | A-337S |
| 14 | 76 | 4400 | yes | CH-35 |

Test V

The devices of Examples 9–14 were tested in fistulated steers in central Indiana during hot summer weather. Some of the steers were lost because of excessive heat. The animals were pastured on improved forage, but it was necessary to supplement their diet with hay and mixed feed because the weather prevented normal forage growth.

Two devices were put in the reticulum of each animal, and were returned to the same position in the rumen or reticulum after being removed for evaluation.

Care was taken to wash impacted feed from inside the caps of the capped devices, without injuring or interfering with the surface of the core. The observed dosage rates of drug from the devices at each measurement interval was as follows. It will be seen that the caps had no important effect on the dosage rates, and that the molecular weight of the polymer had a pronounced effect on the dosage rate.

devices was 2,600. The tubes used in them were 75-mm. lengths of cylindrical seamless type 304 stainless steel tubing, of the same inside and outside diameters used in the examples above. The sealant in Example 15 was Allied CH-35, injected as a hot-melt, and the tubes were not end capped. The sealant in Example 16 was Eastobond A-337S, and the tubes were capped with hemispherical polyurethane caps of the design shown in FIG. 1, and with 38% open area. The devices were assembled as described under Examples 1–6 above.

Test VI

The animals used in this test were not fistulated, and it was therefore not possible to examine the devices at intervals through the test period. Instead, the devices were recovered surgically at intervals through the test. The data obtained in this test, therefore, indicates only the average dosage rate delivered by the devices through the entire period from administration to surgical removal.

The animals were steers which weighed from 675 to 840 pounds when the test began. They were pastured on improved forage in central Indiana during a hot, dry summer, and it was necessary to supplement their diet with hay and mixed feed from time to time. The test was begun by administering two devices to each steer with a balling gun. The steers were maintained with free access to water and were treated for any illnesses which arose during the period of the test.

At the intervals shown in the table below, rumenotomies were performed on some steers and the devices were removed, washed, dried and weighed to determine the amount of medicated core which had eroded away. The results are reported in the table below as the milligrams per day of monensin sodium delivered by the device, expressed as an average over the period from administration to removal of the device. The number of devices removed and weighed at each time interval is shown in parentheses.

TABLE VI

| | CUMULATIVE MEAN RELEASE RATES, MG. MONENSIN SODIUM/DAY ± SD | | | |
|---|---|---|---|---|
| Treatment | 0–42 Days | 0–71 Days | 0–98 Days | 0–126 Days |
| Ex. 9 | 81 ± 2(2) | 97 ± 2(2) | 94 ± 4(4) | (0) |
| Ex. 10 | 48 ± 1(2) | 58 ± 2(2) | 62 ± 2(4) | (0) |
| Ex. 11 | 54 ± 1(2) | 64 ± 1(2) | 66 ± 2(4) | (0) |
| Ex. 12 | 85 ± 1(2) | 98 ± 3(2) | 104 ± 3(4) | (0) |
| Ex. 13 | 54 ± 1(2) | 59 ± 3(2) | 64 ± 2(4) | 69 ± 3(4) |
| Ex. 14 | 56 ± 0(2) | 62 ± 1(2) | 66 ± 3(4) | 67 ± 4(4) |
| Ex. 15 | 90 ± 5(2) | 108 ± 4(2) | 116 ± 5(4) | 128 ± 5(4) |
| Ex. 16 | 101 ± 2(2) | 115 ± 11(2) | 123 ± 12(4) | 127 ± 4(4) |

TABLE V

| | INTERVAL MEAN RELEASE RATES, MG. MONENSIN SODIUM/DAY ± SD | | | | |
|---|---|---|---|---|---|
| | | | OBSERVATION DAY | | |
| Treatment | 28 | 62 | 90 | 119 | 147 |
| Ex. 9 | 58 ± 7(9) | 80 ± 7(9) | 101 ± 21(8) | 125 ± 9(8) | a |
| Ex. 10 | 44 ± 7(4) | 53 ± 4(4) | 71 ± 13(4) | 57 ± 2(3) | 75 ± 5(3) |
| Ex. 11 | 18 ± 7(9) | 64 ± 4(9) | 63 ± 6(8) | 60 ± 10(8) | 77 ± 13(9) |
| Ex. 12 | 52 ± 3(3) | 97 ± 13(3) | 141 ± 9(3) | a | a |
| Ex. 13 | 34 ± 4(5) | 57 ± 5(5) | 63 ± 7(5) | 59 ± 11(5) | 65 ± 8(5) |
| Ex. 14 | 23 ± 7(6) | 56 ± 4(6) | 61 ± 6(6) | 48 ± 10(6) | 74 ± 14(6) |

EXAMPLES 15–16

Two additional lots of devices were made according to the general scheme of Examples 9–14. The number average molecular weight of the polymer used in these The small standard deviations and the consistency of release from one time period to another indicate very excellent reliability of the delivery of drug by these devices. There is a tendency for the release rate to increase as the experiment went on. The rate should increase, because the animals grow larger and require a higher dosage with time. It will also be observed that the devices with polymeric cores of lower molecular weight reliably deliver at higher dosage rates than do those of higher molecular weight polymer.

EXAMPLE 17

A lot of anthelmintic devices was made, containing fenbendazole as the medicament. The drug was 100% pure, and in fine powdered form, and 20% of it was mixed with 80% of polymer, prepared as in Preparation 1 above, having number average molecular weight of 5100. The fenbendazole and polymer were mixed and granulated as described under Examples 1-6 above, and the mixture was extruded and molded into cores as described under Examples 7-8 above, except that the extruder was operated with its feed zone at 18°-38°, its heating zone at 88° and the die at 138°. The cores were cut to 58 mm. length and cooled, and were assembled into 50 mm. type 304 stainless steel cylinders of 30 mm. internal diameter and 35 mm. outside diameter. The sealant was Allied CH-35, injected as a hot-melt, and the protruding ends of the cores and excess sealant were sanded off after the sealant cooled. The ends were then capped with polyethylene hemispherical end caps having 38% open area, of the design shown in FIG. 1.

Test VII

The devices of Example 17 were tested in both intact and fistulated steers. Two devices were administered to each of two fistulated steers with a balling gun, and were removed, washed, dried and weighed at 14-day intervals. The calculated dosage of fenbendazole, based on the weight loss, was as follows.

TABLE VII

| INTERVAL RELEASE RATE, MG. FENBENDAZOLE/DAY ± SD | | | | | | |
|---|---|---|---|---|---|---|
| 0-14 Days | 14-28 Days | 28-42 Days | 42-56 Days | 56-70 Days | 70-87 Days | 87-98 Days |
| 0 | 25 ± 15 | 30 ± 17 | 40 ± 10 | 42 ± 9 | 41 ± 10 | 34 ± 8 |

One device was administered to each of ten intact steers, and the steers were maintained on pasture for 90 days. The devices were then recovered by rumenotomy, five after 62 days and five after 90 days, and were washed, dried and weighed as described above. The cumulative release rate of fenbendazole over 62 days was 25±2 mg./day, and 32±1 mg./day over 90 days.

EXAMPLES 18-21

Four lots of anthelmintic devices were made, using fenbendazole as the medicament. Twenty-five percent of 100% pure, finely powdered fenbendazole was mixed with 75% of polymer, prepared as described in Preparation 1. Two lots of polymer having different molecular weights were used. Examples 18 and 19 used a polymer of number average molecular weight 2730, and Examples 20 and 21, a lot of weight 4275.

The medicament and polymer were mixed, granulated and extruded as described under Example 17 above, and the cores were cut to 58 mm. length. The tubes were 50-mm. lengths of type 304 stainless steel seamless tubing, of the same inside and outside diameters as the tubing used in the examples above. The cores were assembled into the tubes with one of two hot-melt sealants; Examples 18 and 20 used Allied CH-35, and Examples 19 and 21 used Eastobond A-337S. After the ends of the devices were sanded smooth, they were capped with polyurethane hemispherical caps of 38% open area.

Test VIII

The devices of Examples 18-21 were tested in fistulated steers in Indiana, U.S.A. The steers were maintained on improved pasture with unlimited access to water, and were given appropriate care and medication as needed to maintain them in good health. At the intervals shown in the table below, the devices were removed from the animals and washed, dried and weighed as was done in the examples above. The results of the test are reported in the table below as milligrams of fenbendazole released per day, calculated over the interval between weighings.

TABLE VIII

| Observation Day | INTERVAL MEAN RELEASE RATES, MG. FENBENDAZOLE/DAY ± SD | | | |
|---|---|---|---|---|
| | Treatment | | | |
| | Ex. 18 | Ex. 19 | Ex. 20 | Ex. 21 |
| 14 | 22 ± 6(5) | 28 ± 10(5) | | |
| 29 | 83 ± 10(5) | 82 ± 16(5) | 54 ± 5(5) | 64 ± 13(5) |
| 43 | 77 ± 9(5) | 79 ± 26(5) | 43 ± 8(5) | 44 ± 9(5) |
| 55 | 108 ± 12(5) | 108 ± 23(5) | 48 ± 6(5) | 57 ± 12(5) |
| 73 | 102 ± 25(5) | 120 ± 44(5) | 71 ± 7(5) | 66 ± 11(5) |
| 86 | 130 ± 23(5) | 127 ± 35(5) | 74 ± 22(5) | 78 ± 13(5) |
| 107 | (0) | (0) | 50 ± 6(5) | 57 ± 11(5) |

EXAMPLES 22-23

The devices of these examples were 50 mm. long, uncapped, and contained cores comprising 40% of 90.4% pure monensin, sodium salt. The polymer was of the type of Preparation 1 above, and had a number average molecular weight of 3,000. The polymer and finely powdered monensin were mixed, granulated and extruded into cores as described under Examples 7-8 above. The devices were assembled by injecting hot-melt sealant into the annulus; the sealant in Example 22 was Eastobond A-110S, and in Example 23, Allied CH-35. The tubes were type 304 stainless steel cylinders of the size used in the examples above. The devices were faced on an abrasive belt.

Test IX

The devices of Examples 22 and 23 were administered to fistulated steers with a balling gun. Each steer was given two devices, and five devices of each lot were used. The animals were maintained on improved pasture in central Indiana, and were medicated and cared for to keep them in good health through the period of the test. The devices were removed and weighed as described in the examples above, at intervals, and the release rates, calculated over the intervals between observations, were as follows, reported in milligrams of monensin sodium released per day, plus or minus the standard deviation.

(At some intervals, less than all of the devices were weighed, because the operator could not find some in the rumens of the very large fistulated steers.)

TABLE IX

INTERVAL MEAN RELEASE RATES, MG. MONENSIN SODIUM/DAY ± SD

| Observation Day | Treatment Ex. 22 | Ex. 23 |
| --- | --- | --- |
| 28 | 67 ± 4(11) | 81 ± 7(10) |
| 42 | 74 ± 7(11) | 78 ± 11(11) |
| 56 | 96 ± 16(11) | 89 ± 9(11) |
| 73 | 110 ± 15(9) | 84 ± 8(10) |
| 84 | 146 ± 60(10) | 85 ± 13(12) |
| 100 | — | 205 ± 62(10) |

EXAMPLES 24–26

A group of devices were made in 50-mm. type 304 stainless steel seamless tubing having internal diameter of 30 mm. and external diameter of 35 mm. The cores contained 40% of 92.3% pure monensin sodium, and 60% of polymer substantially like that prepared in Preparation 1, but having a number average molecular weight of 3500. The monensin and polymer were mixed, granulated and extruded as described under Examples 7–8. However, some of the cores were extruded to 31 mm. outside diameter and were then machined to 25.4 mm. diameter. The devices made with the machined cores are identified as Example 26; the others used cast cores.

The cores were assembled in tubes with injected hot-melt sealant as has been described in the preceding examples. The sealant was Allied CH-35 in Example 24, and Eastobond A-110S in Examples 25 and 26. The devices were faced on an abrasive belt after assembly to trim the cores to the same length as the tubes. No end caps were used.

Test X

The devices of Examples 24–26 were tested in fistulated cattle which were maintained on improved pasture in central Indiana. The steers were given such care and medication as they needed to keep them in good health. Each animal was administered two devices with a balling gun, and ten devices of each lot were used in the tests. The devices were periodically removed and examined as described in the preceding examples, with the following results.

TABLE X

INTERVAL MEAN RELEASE RATES, MG. MONENSIN SODIUM/DAY ± SD

| Observation Day | Ex. 24 | Ex. 25 | Ex. 26 |
| --- | --- | --- | --- |
| 14 | 46 ± 25(9) | 27 ± 19(9) | 40 ± 16(10) |
| 28 | 105 ± 27(10) | 87 ± 26(9) | 93 ± 19(9) |
| 42 | 98 ± 22(10) | 86 ± 43(9) | 65 ± 25(9) |
| 63 | 94 ± 34(8) | 125 ± 21(9) | 150 ± 32(9) |
| 70 | 129 ± 76(8) | 238 ± 70(9) | 305 ± 96(9) |
| 84 | 122 ± 19(8) | 123 ± 27(8) | 156 ± 52(9) |
| 98 | 85 ± 14(8) | 192 ± 28(8) | 162 ± 24(2) |

EXAMPLES 27–32

A group of six different types of devices were made, using the same cores in each. The polymer was made as in Preparation 1; its number average molecular weight was 3700. Sixty percent of it was mixed with 40% of 87.3% pure monensin sodium. Cores were prepared as described in Examples 1–6, and assembled with Allied CH-35 sealant into the tubes, which were as follows:

| Ex. | |
| --- | --- |
| 27 | low carbon steel |
| 28 | zinc phosphate-dipped low-carbon steel |
| 29 | type 304 stainless steel |
| 30 | nickel-plated low-carbon steel |
| 31 | low-carbon steel coated with epoxy resin |
| 32 | low-carbon steel coated with polyvinyl chloride resin black plastisol |

All tubes were 50 mm. long, 30 mm. inside diameter and 35 mm. outside diameter. Polyurethane end caps having 38% open area were applied as in FIG. 1 and 2 above.

Test XI

The devices of Examples 27–32 were tested in fistulated cattle in central Indiana, U.S.A., during the winter. Two devices were administered orally to each animal. The cattle were maintained on hay and mixed feed, since pasture forage was not available, and were cared for as needed to maintain their health. At intervals, the devices were removed from the animals' reticulums, and dried and weighed as in the tests above. The table below reports the release rates as in the tests above.

TABLE XI

INTERVAL MEAN RELEASE RATES, MG. MONENSIN SODIUM/DAY ± SD

| | Observation Day | | |
| --- | --- | --- | --- |
| | 56 | 84 | 116 |
| Ex. 27 | 81 ± 29(9) | * | * |
| 28 | 71 ± 12(9) | * | * |
| 29 | 42 ± 8(10) | 58 ± 19(10) | 77 ± 8(10) |
| 30 | 44 ± 3(10) | 59 ± 10(10) | 89 ± 7(10) |
| 31 | 42 ± 4(10) | 53 ± 3(10) | 77 ± 5(10) |
| 32 | 44 ± 4(8) | 41 ± 12(8) | 91 ± 18(10) |

*All of Examples 27 and 28 were removed from the test at 56 days because they were failing by hydrolysis of the polymer down the walls of the core.

EXAMPLE 33

A batch of end-capped devices were made, using cores which were prepared, in general, as described in Preparation 1 and Examples 1–6. The number average molecular weight of the polymer was 3700, and 40% of substantially pure monensin sodium was added to the polymer. The tubes were stainless steel, as described in Examples 1–6, and Allied CH-35 sealant was injected into the 2.5 mm. annulus between the tube and core. The ends of the cores were grooved for the retention of polyurethane end-caps of the design shown in FIG. 1.

Test XII

The devices of Example 33 were tested in fistulated cattle which were fed on three different diets, as shown in the table below. At intervals, the devices were removed from the animals' rumens or reticulums, and were dried and weighed as described in the tests above. The table below reports the release rates in the same manner used in the preceeding tests.

TABLE XII

INTERVAL MEAN RELEASE RATES, MG. MONENSIN SODIUM/DAY ± SD

| | Observation Day | | | |
| --- | --- | --- | --- | --- |
| Diet | 0–33 | 33–56 | 56–88 | 88–112 |
| Silage | 34 ± 7 | 69 ± 12 | 78 ± 14 | 118 ± 23 |
| Grain | 24 ± 10 | 68 ± 12 | 46 ± 20 | 156 ± 22 |
| Hay Cubes | 20 ± 5 | 63 ± 9 | 60 ± 10 | 112 ± 16 |

EXAMPLES 34–36

A large number of devices were made according to the general plan of Example 33, except that the number average molecular weight of the polymer was varied as follows: Example 34, 4,000; Example 35, 3,600; and Example 36, 3,200.

Test XIII

The devices of Examples 34–36 were tested in intact cattle on pasture at eight sites in Colorado, Illinois, Nevada, Nebraska, Texas, Kansas, and Indiana. The devices were removed by rumenotomy at certain intervals, and the release of monensin was determined by weight loss as described in the tests above. The data from devices recovered at the various sites have been combined and statistically treated to prepare the tables below. The numbers of devices which are combined in each mean and standard deviation is given in parenthesis after the data. The number of days in each treatment interval is an approximation, to a degree, since not all devices were recovered on the same treatment day. For example, the 0–150 day period actually includes data from devices which were recovered from 149 to 160 days.

TABLE XIII

INTERVAL MEAN RELEASE RATES, MG. MONENSIN SODIUM/DAY ± SD

| Observation Day | Example 34 | Example 35 | Example 36 |
|---|---|---|---|
| 0–56 | 70 ± 6(20) | 80 ± 4(14) | 85 ± 6(14) |
| 0–98 | 77 ± 6(14) | 87 ± 11(17) | 92 ± 5(16) |
| 0–140 | 76 ± 8(14) | 90 ± 8(16) | 90 ± 7(18) |
| 0–150 | | 90 ± 8(48) | |
| 0–175 | | 89 ± 2(72) | |

Test XIV

The tests reported here were carried out by administering devices of Examples 34–36 to intact cattle which were confined and fed various grain and roughage diets, at four sites in Idaho, Nebraska, Nevada and Missouri. The tests were carried out, except for the rations, as described in Test XIII above and the data is presented in the same way.

TABLE XIV

INTERVAL MEAN RELEASE RATES, MG. MONENSIN SODIUM/DAY ± SD

| Observation Day | Example 34 | Example 35 | Example 36 |
|---|---|---|---|
| 0–56 | 63 ± 4(8) | 72 ± 6(8) | 79 ± 3(8) |
| 0–98 | 68 ± 5(8) | 84 ± 5(8) | 88 ± 2(8) |
| 0–140 | 72 ± 6(8) | 82 ± 4(8) | 87 ± 6(8) |
| 0–150 | | 89 ± 9(32) | |

Test XV

Devices of Example 35 were administered to a group of intact cattle which were maintained in central Indiana. Sixty of the devices were administered to cattle on pasture, and twenty of the devices were administered to cattle which were confined and fed grain. The devices were removed after approximately 152 days, and the average payout of monensin was determined by weight loss. The average payout of monensin in the pasture cattle was 94±4 mg/day, and the average payout in the grain-fed cattle was 78±6 mg/day.

We claim:

1. A sustained release drug delivery device for use in the rumen of a ruminant animal which comprises a polymeric core wherein the polymer comprises from about 60% to about 95% of lactic acid and from about 40% to about 5% of glycolic acid and has a number average molecular weight of from about 2000 to about 6000, in which polymer a medicament beneficial when administered to the digestive tract of the ruminant animal is dissolved or suspended, which core is contained in a tube made of material with a density from about 6 to about 10 g./cc. which is compatible with the rumen, which tube has at least one end open for its full diameter, wherein a layer at least 0.7 mm. thick of elastic sealant fills the full length of the annulus between the core and the tube and forms an adhesive bond to both the core and the tube, which sealant is substantially impermeable to water, compatible with both the tube and the core, and compatible with and unaffected by the rumen.

2. A device of claim 1 wherein the sealant is a hot-melt sealant.

3. A device of claim 2 wherein the sealant has a viscosity from about 800 to about 10,000 centipoises at the application temperature.

4. A device of claim 3 wherein the sealant is applied at a temperature from about 120° to about 175° C.

5. A device of claim 4 wherein the sealant comprises ethylene-vinyl acetate copolymer, polyethylene resin, polyamide resin, or thermoplastic rubber.

6. A device of claim 5 wherein the sealant comprises ethylene-vinyl acetate copolymer or polyethylene resin.

7. A device of claim 5 wherein the sealant comprises ethylene-vinyl acetate copolymer.

8. A device of claim 1 wherein the sealant sets or cures chemically.

9. A device of claim 8 wherein the sealant comprises a silicone or a polysulfide.

10. A device of claim 9 wherein the sealant comprises a silicone.

11. A device of claim 1 wherein the number average molecular weight of the polymer comprising the polymeric core is from about 2,000 to about 4,500.

12. A device of claim 11 wherein the number average molecular weight of the polymer comprising the polymeric core is from about 2,500 to about 4,500.

13. A device of claim 2 wherein the number average molecular weight of the polymer comprising the polymeric core is from about 2,000 to about 4,500.

14. A device of claim 13 wherein the number average molecular weight of the polymer comprising the polymeric core is from about 2,500 to about 4,500.

15. A device of claim 4 wherein the number average molecular weight of the polymer comprising the polymeric core is from about 2,500 to about 4,500.

16. A device of claim 6 wherein the number average molecular weight of the polymer comprising the polymeric core is from about 2,500 to about 4,500.

17. A device of claim 8 wherein the number average molecular weight of the polymer comprising the polymeric core is from about 2,500 to about 4,500.

18. A device of claim 11 wherein the polymeric core comprises from about 1 to about 50% of medicament.

19. A device of claim 12 wherein the polymeric core comprises from about 1 to about 50% of medicament.

20. A device of claim 18 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

21. A device of claim 20 wherein the medicament is a ruminant feed efficiency improver, an anthelmintic, an antibiotic, an ectoparasiticide, a trace element, a nutritional agent, or a combination thereof.

22. A device of claim 21 wherein the medicament is a ruminant feed efficiency improver, an anthelmintic, an antibiotic or a combination thereof.

23. A device of claim 22 wherein the medicament is a ruminant feed efficiency improver, an anthelmintic, or a combination thereof.

24. A device of claim 23 wherein the medicament is monensin, narasin, salinomycin, lasalocid, fenbendazole or a combination thereof.

25. A device of claim 24 wherein the medicament is monensin, fenbendazole or a combination thereof.

26. A device of claim 20 wherein the medicament is monensin, narasin, salinomycin, melengestrol, ivermectin or a combination thereof.

27. A device of claim 4 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

28. A device of claim 27 wherein the medicament is a ruminant feed efficiency improver, an anthelmintic, an antibiotic or a combination thereof.

29. A device of claim 28 wherein the medicament is monensin, fenbendazole or a combination thereof.

30. A device of claim 27 wherein the medicament is monensin, narasin, salinomycin, melengestrol, ivermectin or a combination thereof.

31. A device of claim 6 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

32. A device of claim 31 wherein the medicament is a ruminant feed efficiency improver, an anthelmintic, an antibiotic or a combination thereof.

33. A device of claim 32 wherein the medicament is monensin, fenbendazole or a combination thereof.

34. A device of claim 31 wherein the medicament is monensin, narasin, salinomycin, melengestrol, ivermectin or a combination thereof.

35. A device of claim 8 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

36. A device of claim 35 wherein the medicament is a ruminant feed efficiency improver, an anthelmintic, an antibiotic or a combination thereof.

37. A device of claim 36 wherein the medicament is monensin, fenbendazole or a combination thereof.

38. A device of claim 35 wherein the medicament is monensin, narasin, salinomycin, melengestrol, ivermectin or a combination thereof.

39. A device of claim 14 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

40. A device of claim 39 wherein the medicament is a ruminant feed efficiency improver, an anthelmintic, an antibiotic or a combination thereof.

41. A device of claim 40 wherein the medicament is monensin, fenbendazole or a combination thereof.

42. A device of claim 39 wherein the medicament is monensin, narasin, salinomycin, melengestrol, ivermectin or a combination thereof.

43. A device of claim 15 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

44. A device of claim 43 wherein the medicament is a ruminant feed efficiency improver, an anthelmintic, an antibiotic or a combination thereof.

45. A device of claim 44 wherein the medicament is monensin, narasin, salinomycin, lasalocid, fenbendazole or a combination thereof.

46. A device of claim 45 wherein the medicament is monensin, fenbendazole or a combination thereof.

47. A device of claim 43 wherein the medicament is monensin, narasin, salinomycin, melengestrol, ivermectin or a combination thereof.

48. A device of claim 16 wherein the medicament is a ruminant feed efficiency improver, an anthelmintic, an antibiotic, a coccidiostat, an ectoparasiticide, a feed-through insecticide, an estrus suppressor, a trace element, a nutritional agent, or a combination thereof.

49. A device of claim 48 wherein the medicament is a ruminant feed efficiency improver, an anthelmintic, an antibiotic, or a combination thereof.

50. A device of claim 49 wherein the medicament is monensin, narasin, salinomycin, lasalocid, fenbendazole or a combination thereof.

51. A device of claim 50 wherein the medicament is monensin, fenbendazole or a combination thereof.

52. A device of claim 48 wherein the medicament is monensin, narasin, salinomycin, melengestrol, ivermectin or a combination thereof.

53. A device of claim 2 wherein the tube is cylindrical.

54. A device of claim 53 wherein both ends of the tube are open for its full diameter.

55. A device of claim 54 wherein the tube is made of a ferrous alloy.

56. A device of claim 55 wherein the tube is made of stainless steel or of low-carbon steel coated with a film compatible with the sealant and with the rumen.

57. A device of claim 56 wherein the length of the tube is substantially the same as the length of the core.

58. A device of claim 57 wherein the wall of the tube is from about 1 to about 4 millimeters thick.

59. A device of claim 58 wherein the wall of the tube is from about 2 to about 3 millimeters thick.

60. A device of claim 57 wherein the wall of the tube is from about 1 to about 3 millimeters thick.

61. A device of claim 58 wherein the length of the tube and core is from about 25 to about 85 millimeters, and the outside diameter of the tube is from about 10 to about 40 millimeters.

62. A device of claim 61 wherein the open ends are covered with perforated end caps.

63. A device of claim 62 wherein the end caps are molded of elastomeric material and are approximately hemispherical in shape.

64. A device of claim 63 wherein the open ends are circumferentially grooved and the end cap is lipped to engage the groove.

65. A device of claim 62 wherein the end caps are an extension of the material of the tube.

66. A device of claim 62 wherein the end caps are integral parts of an outer shell enclosing the tube.

67. A device of claim 4 wherein the tube is cylindrical and has both ends open for its full diameter.

68. A device of claim 67 wherein the tube is made of stainless steel or of low-carbon steel coated with a film compatible with the sealant and with the rumen.

69. A device of claim 68 wherein the tube is substantially the same length as the core.

70. A device of claim 69 wherein the wall of the tube is from about 1 to about 4 millimeters thick, the length of the tube is from about 25 to about 85 millimeters, and the outside diameter of the tube is from about 10 to about 40 millimeters.

71. A device of claim 70 wherein the open ends of the tube are covered with molded elastomeric approximately hemispherical perforated end caps, and the ends of the tube are circumferentially grooved and the end caps are lipped to engage the groove.

72. A device of claim 70 wherein the open ends of the tube are covered with perforated end caps which are an extension of the material of the tube.

73. A device of claim 70 wherein the open ends of the tube are covered with perforated end caps which are integral parts of an outer shell enclosing the tube.

74. A device of claim 6 wherein the tube is cylindrical and has both ends open for its full diameter.

75. A device of claim 74 wherein the tube is made of stainless steel or of low-carbon steel coated with a film compatible with the sealant and with the rumen.

76. A device of claim 75 wherein the tube is substantially the same length as the core.

77. A device of claim 76 wherein the walls of the tube are from about 1 to about 4 millimeters thick, the length of the tube is from about 25 to about 85 millimeters, and the outside diameter of the tube is from about 10 to about 40 millimeters.

78. A device of claim 77 wherein the ends of the tube are covered with molded elastomeric approximately hemispherical perforated end caps, the ends of the tube are circumferentially grooved and the cap is lipped to engage the groove.

79. A device of claim 77 wherein the open ends of the tube are covered with perforated end caps which are an extension of the material of the tube.

80. A device of claim 77 wherein the open ends of the tube are covered with perforated end caps which are integral parts of an outer shell enclosing the tube.

81. A device of claim 8 wherein the tube is cylindrical and has both ends open for its full diameter.

82. A device of claim 81 wherein the tube is made of stainless steel or of low-carbon steel coated with a film compatible with the sealant and with the rumen.

83. A device of claim 82 wherein the tube is substantially the same length as the core, its walls are from about 1 to about 4 millimeters thick, its length is from about 25 to about 85 millimeters, and its outside diameter is from about 10 to about 40 millimeters.

84. A device of claim 83 wherein the ends of the tube are covered with molded elastomeric approximately hemispherical perforated end caps, the ends of the tube are circumferentially grooved and the cap is lipped to engage the groove.

85. A device of claim 83 wherein the open ends of the tube are covered with perforated end caps which are an extension of the material of the tube.

86. A device of claim 83 wherein the open ends of the tube are covered with perforated end caps which are integral parts of an outer shell enclosing the tube.

87. A device of claim 12 wherein the tube is cylindrical and has both ends open for its full diameter.

88. A device of claim 87 wherein the tube is made of stainless steel or of low-carbon steel coated with a film compatible with the sealant and with the rumen.

89. A device of claim 88 wherein the tube is substantially the same length as the core, its walls are from about 1 to about 4 millimeters thick, its length is from about 25 to about 85 millimeters, and its outside diameter is from about 10 to about 40 millimeters.

90. A device of claim 89 wherein the ends of the tube are covered with molded elastomeric approximately hemispherical perforated end caps, the ends of the tube are circumferentially grooved and the cap is lipped to engage the groove.

91. A device of claim 89 wherein the open ends of the tube are covered with perforated end caps which are an extension of the material of the tube.

92. A device of claim 89 wherein the open ends of the tube are covered with perforated end caps which are integral parts of an outer shell enclosing the tube.

93. A device of claim 14 wherein the tube is cylindrical and has both ends open for its full diameter.

94. A device of claim 93 wherein the tube is made of stainless steel or of low-carbon steel coated with a film compatible with the sealant and with the rumen.

95. A device of claim 94 wherein the tube is substantially the same length as the core, its walls are from about 1 to about 4 millimeters thick, its length is from about 25 to about 85 millimeters, and its outside diameter is from about 10 to about 40 millimeters.

96. A device of claim 95 wherein the ends of the tube are covered with molded elastomeric approximately hemispherical perforated end caps, the ends of the tube are circumferentially grooved and the cap is lipped to engage the groove.

97. A device of claim 95 wherein the open ends of the tube are covered with perforated end caps which are an extension of the material of the tube.

98. A device of claim 95 wherein the open ends of the tube are covered with perforated end caps which are integral parts of an outer shell enclosing the tube.

99. A device of claim 16 wherein the tube is cylindrical and has both ends open for its full diameter.

100. A device of claim 99 wherein the tube is made of stainless steel or of low-carbon steel coated with a film compatible with the sealant and with the rumen.

101. A device of claim 100 wherein the tube is substantially the same length as the core, its walls are from about 1 to about 4 millimeters thick, its length is from about 25 to about 85 millimeters, and its outside diameter is from about 10 to about 40 millimeters.

102. A device of claim 101 wherein the ends of the tube are covered with molded elastomeric approximately hemispherical perforated end caps, the ends of the tube are circumferentially grooved and the cap is lipped to engage the groove.

103. A device of claim 101 wherein the open ends of the tube are covered with perforated end caps which are an extension of the material of the tube.

104. A device of claim 101 wherein the open ends of the tube are covered with perforated end caps which are integral parts of an outer shell enclosing the tube.

105. A device of claim 20 wherein the tube is cylindrical and has both ends open for its full diameter.

106. A device of claim 105 wherein the tube is made of stainless steel or of low-carbon steel coated with a film compatible with the sealant and with the rumen.

107. A device of claim 106 wherein the length of the tube is substantially the same as that of the core.

108. A device of claim 107 wherein the walls of the tube are from about 1 to about 4 millimeters thick, the length of the tube is from about 25 to about 85 millimeters, and the outside diameter of the tube is from about 10 to about 40 millimeters.

109. A device of claim 108 wherein the ends of the tube are covered with molded elastomeric approximately hemispherical perforated end caps, the ends of the tube are circumferentially grooved and the cap is lipped to engage the groove.

110. A device of claim 108 wherein the open ends of the tube are covered with perforated end caps which are an extension of the material of the tube.

111. A device of claim 108 wherein the open ends of the tube are covered with perforated end caps which are integral parts of an outer shell enclosing the tube.

112. A device of claim 27 wherein the tube is cylindrical and has both ends open for its full diameter.

113. A device of claim 112 wherein the tube is made of stainless steel or of low-carbon steel coated with a film compatible with the sealant and with the rumen.

114. A device of claim 113 wherein the tube is substantially the same length as the core, its walls are from about 1 to about 4 millimeters thick, its length is from about 25 to about 85 millimeters, and its outside diameter is from about 10 to about 40 millimeters.

115. A device of claim 114 wherein the ends of the tube are covered with molded elastomeric approximately hemispherical perforated end caps, the ends of the tube are circumferentially grooved and the cap is lipped to engage the groove.

116. A device of claim 114 wherein the open ends of the tube are covered with perforated end caps which are an extension of the material of the tube.

117. A device of claim 114 wherein the open ends of the tube are covered with perforated end caps which are integral parts of an outer shell enclosing the tube.

118. A device of claim 31 wherein the tube is cylindrical and has both ends open for its full diameter.

119. A device of claim 118 wherein the tube is made of stainless steel or of low-carbon steel coated with a film compatible with the sealant and with the rumen.

120. A device of claim 119 wherein the tube is substantially the same length as the core, its walls are from about 1 to about 4 millimeters thick, its length is from about 25 to about 85 millimeters, and its outside diameter is from about 10 to about 40 millimeters.

121. A device of claim 120 wherein the ends of the tube are covered with molded elastomeric approximately hemispherical perforated end caps, the ends of the tube are circumferentially grooved and the cap is lipped to engage the groove.

122. A device of claim 120 wherein the open ends of the tube are covered with perforated end caps which are an extension of the material of the tube.

123. A device of claim 120 wherein the open ends of the tube are covered with perforated end caps which are integral parts of an outer shell enclosing the tube.

124. A device of claim 33 wherein the tube is cylindrical and has both ends open for its full diameter.

125. A device of claim 124 wherein the tube is made of stainless steel or of low-carbon steel coated with a film compatible with the sealant and with the rumen.

126. A device of claim 125 wherein the tube is substantially the same length as the core, its walls are from about 1 to about 4 millimeters thick, its length is from about 25 to about 85 millimeters, and its outside diameter is from about 10 to about 40 millimeters.

127. A device of claim 126 wherein the ends of the tube are covered with molded elastomeric approximately hemispherical perforated end caps, the ends of the tube are circumferentially grooved and the cap is lipped to engage the groove.

128. A device of claim 126 wherein the open ends of the tube are covered with perforated end caps which are an extension of the material of the tube.

129. A device of claim 126 wherein the open ends of the tube are covered with perforated end caps which are integral parts of an outer shell enclosing the tube.

130. A device of claim 35 wherein the tube is cylindrical and has both ends open for its full diameter.

131. A device of claim 130 wherein the tube is made of stainless steel or of low-carbon steel coated with a film compatible with the sealant and with the rumen.

132. A device of claim 131 wherein the tube is substantially the same length as the core, its walls are from about 1 to about 4 millimeters thick, its length is from about 25 to about 85 millimeters, and its outside diameter is from about 10 to about 40 millimeters.

133. A device of claim 132 wherein the ends of the tube are covered with molded elastomeric approximately hemispherical perforated end caps, the ends of the tube are circumferentially grooved and the cap is lipped to engage the groove.

134. A device of claim 132 wherein the open ends of the tube are covered with perforated end caps which are an extension of the material of the tube.

135. A device of claim 132 wherein the open ends of the tube are covered with perforated end caps which are integral parts of an outer shell enclosing the tube.

136. A device of claim 39 wherein the tube is cylindrical and has both ends open for its full diameter.

137. A device of claim 136 wherein the tube is made of stainless steel or of low-carbon steel coated with a film compatible with the sealant and with the rumen.

138. A device of claim 137 wherein the tube is substantially the same length as the core, its walls are from about 1 to about 4 millimeters thick, its length is from about 25 to about 85 millimeters, and its outside diameter is from about 10 to about 40 millimeters.

139. A device of claim 138 wherein the ends of the tube are covered with molded elastomeric approximately hemispherical perforated end caps, the ends of the tube are circumferentially grooved and the cap is lipped to engage the groove.

140. A device of claim 138 wherein the open ends of the tube are covered with perforated end caps which are an extension of the material of the tube.

141. A device of claim 138 wherein the open ends of the tube are covered with perforated end caps which are integral parts of an outer shell enclosing the tube.

142. A device of claim 41 wherein the tube is cylindrical and has both ends open for its full diameter.

143. A device of claim 142 wherein the tube is made of stainless steel or of low-carbon steel coated with a film compatible with the sealant and with the rumen.

144. A device of claim 143 wherein the tube is substantially the same length as the core, its walls are from about 1 to about 4 millimeters thick, its length is from about 25 to about 85 millimeters, and its outside diameter is from about 10 to about 40 millimeters.

145. A device of claim 144 wherein the ends of the tube are covered with molded elastomeric approximately hemispherical perforated end caps, the ends of the tube are circumferentially grooved and the cap is lipped to engage the groove.

146. A device of claim 144 wherein the open ends of the tube are covered with perforated end caps which are an extension of the material of the tube.

147. A device of claim 144 wherein the open ends of the tube are covered with perforated end caps which are integral parts of an outer shell enclosing the tube.

148. A device of claim 43 wherein the tube is cylindrical and has both ends open for its full diameter.

149. A device of claim 148 wherein the tube is made of stainless steel or of low-carbon steel coated with a film compatible with the sealant and with the rumen.

150. A device of claim 149 wherein the tube is substantially the same length as the core, its walls are from about 1 to about 4 millimeters thick, its length is from about 25 to about 85 millimeters, and its outside diameter is from about 10 to about 40 millimeters.

151. A device of claim 150 wherein the ends of the tube are covered with molded elastomeric approximately hemispherical perforated end caps, the ends of the tube are circumferentially grooved and the cap is lipped to engage the groove.

152. A device of claim 150 wherein the open ends of the tube are covered with perforated end caps which are an extension of the material of the tube.

153. A device of claim 150 wherein the open ends of the tube are covered with perforated end caps which are integral parts of an outer shell enclosing the tube.

154. A device of claim 48 wherein the tube is cylindrical and has both ends open for its full diameter.

155. A device of claim 154 wherein the tube is made of stainless steel or of low-carbon steel coated with a film compatible with the sealant and with the rumen.

156. A device of claim 155 wherein the tube is substantially the same length as the core, its walls are from about 1 to about 4 millimeters thick, its length is from about 25 to about 85 millimeters, and its outside diameter is from about 10 to about 40 millimeters.

157. A device of claim 156 wherein the ends of the tube are covered with molded elastomeric approximately hemispherical perforated end caps, the ends of the tube are circumferentially grooved and the cap is lipped to engage the groove.

158. A device of claim 156 wherein the open ends of the tube are covered with perforated end caps which are an extension of the material of the tube.

159. A device of claim 156 wherein the open ends of the tube are covered with perforated end caps which are integral parts of an outer shell enclosing the tube.

160. A device of claim 50 wherein the tube is cylindrical and has both ends open for its full diameter.

161. A device of claim 160 wherein the tube is made of stainless steel or of low-carbon steel coated with a film compatible with the sealant and with the rumen.

162. A device of claim 161 wherein the tube is substantially the same length as the core, its walls are from about 1 to about 4 millimeters thick, its length is from about 25 to about 85 millimeters, and its outside diameter is from about 10 to about 40 millimeters.

163. A device of claim 162 wherein the ends of the tube are covered with molded elastomeric approximately hemispherical perforated end caps, the ends of the tube are circumferentially grooved and the cap is lipped to engage the groove.

164. A device of claim 162 wherein the open ends of the tube are covered with perforated end caps which are an extension of the material of the tube.

165. A device of claim 162 wherein the open ends of the tube are covered with perforated end caps which are integral parts of an outer shell enclosing the tube.

166. A device of claim 51 wherein the tube is cylindrical and has both ends open for its full diameter.

167. A device of claim 166 wherein the tube is made of stainless steel or of low-carbon steel coated with a film compatible with the sealant and with the rumen.

168. A device of claim 167 wherein the tube is substantially the same length as the core, its walls are from about 1 to about 4 millimeters thick, its length is from about 25 to about 85 millimeters, and its outside diameter is from about 10 to about 40 millimeters.

169. A device of claim 168 wherein the ends of the tube are covered with molded elastomeric approximately hemispherical perforated end caps, the ends of the tube are circumferentially grooved and the cap is lipped to engage the groove.

170. A device of claim 168 wherein the open ends of the tube are covered with perforated end caps which are an extension of the material of the tube.

171. A device of claim 168 wherein the open ends of the tube are covered with perforated end caps which are integral parts of an outer shell enclosing the tube.

172. A device of claim 52 wherein the tube is cylindrical and has both ends open for its full diameter.

173. A device of claim 172 wherein the tube is made of stainless steel or of low-carbon steel coated with a film compatible with the sealant and with the rumen.

174. A device of claim 173 wherein the tube is substantially the same length as the core, its walls are from about 1 to about 4 millimeters thick, its length is from about 25 to about 85 millimeters, and its outside diameter is from about 10 to about 40 millimeters.

175. A device of claim 174 wherein the ends of the tube are covered with molded elastomeric approximately hemispherical perforated end caps, the ends of the tube are circumferentially grooved and the cap is lipped to engage the groove.

176. A device of claim 174 wherein the open ends of the tube are covered with perforated end caps which are an extension of the material of the tube.

177. A device of claim 174 wherein the open ends of the tube are covered with perforated end caps which are integral parts of an outer shell enclosing the tube.

* * * * *

UNITED STATES PATENT AND TRADEMARK OFFICE
CERTIFICATE OF CORRECTION

PATENT NO. : 4,649,042

DATED : March 10, 1987

INVENTOR(S) : Robert C. Davis, et al.

It is certified that error appears in the above—identified patent and that said Letters Patent is hereby corrected as shown below:

Column 17, line 28, insert -- and -- after "annulus".

Column 20, Table I, in the heading, insert a "/" between the words "SODIUM" and "DAY".

Column 22, Table III, in the heading, insert a "/" between the words "SODIUM" and "DAY".

Signed and Sealed this

First Day of September, 1987

Attest:

DONALD J. QUIGG

Attesting Officer

Commissioner of Patents and Trademarks